(12) United States Patent
Morimoto et al.

(10) Patent No.: US 9,050,403 B2
(45) Date of Patent: Jun. 9, 2015

(54) PLATELET-RICH PLASMA SEPARATOR AND PLATELET-RICH PLASMA SEPARATION METHOD

(75) Inventors: Shinji Morimoto, Osaka (JP); Norihisa Sasayama, Osaka (JP); Akio Shirasu, Osaka (JP)

(73) Assignee: NIPRO CORPORATION, Osaka (JP)

( * ) Notice: Subject to any disclaimer, the term of this patent is extended or adjusted under 35 U.S.C. 154(b) by 1027 days.

(21) Appl. No.: 12/311,533

(22) PCT Filed: Oct. 19, 2007

(86) PCT No.: PCT/JP2007/070459
§ 371 (c)(1),
(2), (4) Date: Apr. 2, 2009

(87) PCT Pub. No.: WO2008/050688
PCT Pub. Date: May 2, 2008

(65) Prior Publication Data
US 2010/0025342 A1    Feb. 4, 2010

(30) Foreign Application Priority Data

Oct. 27, 2006    (JP) .................. 2006-292821

(51) Int. Cl.
| | |
|---|---|
| B01D 29/00 | (2006.01) |
| A61M 1/02 | (2006.01) |
| A61B 5/15 | (2006.01) |
| A61K 35/16 | (2006.01) |
| A61M 5/315 | (2006.01) |
| A61M 5/31 | (2006.01) |

(52) U.S. Cl.
CPC .............. *A61M 1/029* (2013.01); *A61B 5/1416* (2013.01); *A61K 35/16* (2013.01);
(Continued)

(58) Field of Classification Search
None
See application file for complete search history.

(56) References Cited

U.S. PATENT DOCUMENTS

| 4,936,315 A * | 6/1990 | Lineback ...................... 600/578 |
| 6,123,687 A | 9/2000 | Simonyi et al. |

(Continued)

FOREIGN PATENT DOCUMENTS

| JP | 2002-504401 | 2/2002 |
| JP | 2002-204906 | 7/2002 |

(Continued)

OTHER PUBLICATIONS

Dental and Craniofacial Applications of Platelet-Rich Plasma—by Robert E. Marx, Arun K. Garg—published by Quintessence Publishing Co., Ind.—on Feb. 10, 2006.

*Primary Examiner* — Dirk Bass
(74) *Attorney, Agent, or Firm* — Jordan and Hamburg LLP

(57) ABSTRACT

Provided is a platelet-rich plasma separator which can carry out the separation of a platelet-rich plasma with a small number of gamma radiation sterilized instruments and a platelet-rich plasma separation method. The platelet-rich plasma separator comprises a first syringe and a second syringe. The first syringe comprises a first syringe cylinder provided with a first port on which a blood collection needle can be mounted, a first cap detachable from the first port, a first gasket for sealing the first syringe cylinder fluid-tightly, which first gasket is reciprocated within the first syringe cylinder, and a first plunger provided detachably on the first gasket. The second syringe comprises a first hollow needle, which can be passed through the first gasket, a second syringe cylinder having a second port on which the first hollow needle can be mounted, a second cap detachable from the second port, a second gasket for sealing the second syringe cylinder liquid-tightly, which second gasket is reciprocated within the second syringe cylinder, and a second plunger provided detachable on the second gasket.

6 Claims, 14 Drawing Sheets

(52) U.S. Cl.
CPC ... *A61M 5/31511* (2013.01); *A61M 2005/3104* (2013.01); *A61M 2005/3106* (2013.01); *A61M 2005/31598* (2013.01); *A61M 2202/0427* (2013.01)

(56) References Cited

U.S. PATENT DOCUMENTS

| | | | |
|---|---|---|---|
| 6,716,187 B1 * | 4/2004 | Jorgensen et al. | 604/6.05 |
| 2004/0167004 A1 | 8/2004 | Jorgensen et al. | |
| 2007/0075016 A1 * | 4/2007 | Leach | 210/516 |

FOREIGN PATENT DOCUMENTS

| | | |
|---|---|---|
| JP | 2005-278910 | 10/2005 |
| JP | 2006-078428 | 3/2006 |
| JP | 2006-232834 | 9/2006 |
| WO | WO-2006/030749 | 3/2006 |

\* cited by examiner

PLATELET-RICH PLASMA SEPARATOR AND PLATELET-RICH PLASMA SEPARATION METHOD

TECHNICAL FIELD

The present invention relates to a platelet-rich plasma separator having a syringe used to aspirate blood and a syringe used to aspirate a centrifuged section containing platelets and plasma from the syringe and to a platelet-rich plasma separation method.

BACKGROUND ART

Platelet-rich plasma (hereafter also referred to as "PRP") is plasma containing a large number of platelets. Whole blood, which contains corpuscle components, contains approximately 95% red blood cells, 3% white blood cells, and approximately 1% platelets. On the other hand, platelet-rich plasma contains a higher proportion of platelets. There is no specific definition of the proportion of platelets in PRP. Taking into consideration that the proportion of plasma in whole blood is, in general, approximately 55%, the proportion of platelets in plasma from which the corpuscle components have been removed is assumed to be approximately 2%. PRP contains a clearly higher proportion of platelets than this approximate 2%.

PRP is obtained by centrifuging whole blood. In detail, first, red blood cells are separated from the whole blood by weak centrifugation to obtain plasma. This plasma contains white blood cells and platelets. Then the plasma is further subjected to strong centrifugation. As a result, platelets are concentrated in the direction to which centrifugal force is applied (hereafter also referred to as centrifugal direction), leaving almost no platelets in supernatant. Then PRP is obtained by removing the supernatant from the plasma which has undergone strong centrifugation, or by taking out only the predetermined amount of the plasma from the part in the centrifugal direction (lower part) (see Patent Publication 1).

It is known that growth factors, such as PDGF, TGF-beta, and ILGF, exist in alpha granules of platelets. It is noted that these growth factors play an effective part in healing of wound and tissue regeneration. For example, PRP is expected to be used in regeneration medicine, such as periodontal-tissue-regeneration methods. (See Patent Publication 2, Patent Publication 3, and Nonpatent Literature 1).
Patent Publication 1: JP, 2006-78428,A
Patent Publication 2: JP, 2006-232834,A
Patent Publication 3: JP, 2005-278910,A
Nonpatent Literature 1: "Dental And Craniofacial Applications Of Platelet-Rich Plasma" by Robert E. Marx, Quintessence Publishing Co, Inc.

SUMMARY OF THE INVENTION

When using PRP in regeneration medicine, it is required that all the instruments with which PRP is prepared should be sterilized by gamma radiation from a viewpoint of safety. However, there is a problem that if a container with a rubber plug, such as the vacuum blood collection tube described in Patent Publication 1, is sterilized by gamma radiation, the rubber plug gets deteriorated. Degradation of the rubber plug can cause exudation of additives from the plug or the fractured or chipped plug, leaving a risk of contamination of such chipped pieces into blood or PRP.

The present invention has been made in consideration of these problems, and is intended to provide a platelet-rich plasma separation method which can carry out the separation of platelet-rich plasma with a small number of gamma radiation sterilized instruments and a platelet-rich plasma separator.

(1) A platelet-rich plasma separator according to the present invention comprises a first syringe used to aspirate blood, and a second syringe used to aspirate a centrifuged section containing platelets and plasma from the first syringe. Said first syringe comprises a first syringe cylinder having a first port on which a blood collection needle can be mounted, a first cap detachable from said first port, a first gasket for sealing said first syringe cylinder liquid-tightly, which first gasket is reciprocated within the first syringe cylinder, and a first plunger provided detachably on said first gasket. Said second syringe comprises a first hollow needle, which can be passed through said first gasket, a second syringe cylinder having a second port on which said first hollow needle can be mounted, a second cap detachable from said second port, a second gasket for sealing said second syringe cylinder liquid-tightly, which second gasket is reciprocated within the second syringe cylinder, and a second plunger provided detachably on said second gasket.

The first syringe is used for blood collection with a blood collection needle mounted on. The fact that a blood collection needle can be mounted on the first port includes an aspect where the blood collection needle is directly mounted on the first port or an aspect where the blood collection needle is mounted on the first port via other members, such as an extension tube. The first syringe cylinder is filled with blood (whole blood) through blood collection. The blood collection needle is removed from the first syringe cylinder, and then the first port is sealed with the first cap. Thereby, the blood is hermetically sealed in the first syringe cylinder. Then the first plunger is removed from the first gasket. The first syringe cylinder is centrifuged in this state. By the centrifugation, the blood is separated into a red blood cell fraction (the first section) and a plasma fraction (the second section) containing white blood cells and platelets. In this centrifugation, the red blood cell fraction is separated toward the first-port side and the plasma fraction is separated toward the first-gasket side in the first syringe cylinder.

The second syringe is used for suction of the plasma fraction from the centrifuged first syringe cylinder. The fact that a first hollow needle can be mounted on the second port includes an aspect where the first hollow needle is directly mounted on the second port or an aspect where the first hollow needle is mounted on the second port via other members, such as an extension tube. When the first hollow needle is directly mounted on the second port, for example, the second syringe is advanced into the first syringe cylinder, and then the first hollow needle is passed through the first gasket. When the first hollow needle is mounted on the second port via an extension tube, the first hollow needle and the extension tube are advanced into the first syringe cylinder, and then the first hollow needle is passed through the first gasket. The tip of the first hollow needle reaches the inside of the plasma fraction on the side of the first gasket. When the second plunger of the second syringe is pulled outwardly, the second gasket is moved within the second syringe cylinder, whereby the plasma fraction is aspirated into the second syringe cylinder through the first hollow needle.

After the plasma fraction has been aspirated, the first hollow needle along with the second syringe or the first hollow needle along with the extension tube is pulled out of the first syringe cylinder. The first hollow needle is removed from the second syringe cylinder, and then the second port is sealed with the second cap. Thereby, the plasma fraction is hermetically sealed in the second syringe cylinder. Then the second plunger is removed from the second gasket. The second syringe cylinder is centrifuged in this state. By the centrifugation, the plasma fraction is separated into an upper portion (second gasket side) substantially consisting only of the supernatant, that is, the plasma component, and a lower portion (second-port side) containing platelet-rich plasma containing a large number of platelets. The second cap is removed from the second syringe cylinder, the second plunger is mounted on the second gasket, and then the platelet-rich plasma is discharged from the second port of the second syringe cylinder.

(2) Said first plunger is preferably detachable from said first gasket in a threaded fashion. Said second plunger is preferably detachable from said second gasket in a threaded fashion. Thereby, the first plunger or the second plunger detachable from the first gasket or the second gasket, respectively, is realized in a simple manner. Moreover, the first plunger or the second plunger can be repeatedly attached/detached to/from the first gasket or the second gasket, respectively.

(3) Said first gasket may have a guide hole on the side to/from which said first plunger is attached/detached. Said second syringe cylinder may have, around the second port, a guide piece to be fitted in said guide hole.

When the second syringe is advanced into the first syringe cylinder, the guide piece of the second syringe cylinder is fitted in the guide hole of the first gasket. Thereby, the second syringe cylinder and the first gasket are fitted with each other. As described above, when the second plunger is pulled outwardly from the second syringe cylinder, the plasma fraction in the first syringe cylinder is aspirated into the second syringe cylinder. Accordingly, the first gasket is moved within the first syringe cylinder toward the first-port side. The second syringe cylinder is further advanced into the first syringe cylinder with the movement of the first gasket. Thereby, the suction of the plasma fraction from the first syringe cylinder into the second syringe cylinder is performed smoothly.

(4) Said first syringe and said second syringe are preferably provided in a hermetically sealed sterilized package. Provision of these as a kit hermetically sealed in a sterilized package would improve user-friendliness.

(5) A platelet-rich plasma separator according to the invention comprises a third syringe used to aspirate blood, a fourth syringe used to aspirate a centrifuged section containing platelets and plasma from the third syringe. Said third syringe comprises a third syringe cylinder having a third port on which a blood collection needle can be mounted, a third cap detachable from said third port, a third gasket for sealing said third syringe cylinder liquid-tightly, which third gasket is reciprocated within the third syringe cylinder, a first split plunger provided on said third gasket and having an insertion hole that communicates with the third gasket, and a second split plunger detachably connected to said first split plunger. Said fourth syringe comprises a second hollow needle that can be passed via the insertion hole of said first split plunger through said third gasket, a fourth syringe cylinder having a fourth port on which said second hollow needle can be mounted, a fourth cap detachable from said fourth port, a fourth gasket for sealing said fourth syringe cylinder liquid-tightly, which fourth gasket is reciprocated within the fourth syringe cylinder, and a fourth plunger provided detachably on said fourth gasket.

The third syringe is used for blood collection with a blood collection needle mounted on. The fact that a blood collection needle can be mounted on the third port includes an aspect where the blood collection needle is directly mounted on the third port or an aspect where the blood collection needle is mounted on the third port via other members, such as an extension tube. The third syringe cylinder is filled with blood (whole blood) through blood collection. The blood collection needle is removed from the third syringe cylinder, and then the third port is sealed with the third cap. Thereby, the blood is hermetically sealed in the third syringe cylinder. Then the second split plunger is removed from the first split plunger. The third syringe cylinder is centrifuged in this state. By the centrifugation, the blood is separated into a red blood cell fraction (the first section) and a plasma fraction (the second section) containing white blood cells and platelets. In this centrifugation, the red blood cell fraction is separated toward the third-port side and the plasma fraction is separated toward the third-gasket side in the third syringe cylinder.

The fourth syringe is used for suction of the plasma fraction from the centrifuged third syringe cylinder. The fact that a second hollow needle can be mounted on the fourth port includes an aspect where the second hollow needle is directly mounted on the fourth port or an aspect where the second hollow needle is mounted on the fourth port via other members, such as an extension tube. When the second hollow needle is directly mounted on the fourth port, for example, the fourth syringe is advanced into the third syringe cylinder, and then the second hollow needle reaches the insertion hole of the first split plunger and is further passed through the third gasket. When the second hollow needle is mounted on the fourth port via an extension tube, the second hollow needle and the extension tube are advanced into the third syringe cylinder, and then the second hollow needle reaches the insertion hole of the first split plunger and is further passed through the third gasket. Thereby, the tip of the second hollow needle reaches the inside of the plasma fraction on the third gasket side in the third syringe cylinder. When the fourth plunger of the fourth syringe is pulled outwardly, the fourth gasket is moved within the fourth syringe cylinder, whereby the plasma fraction is aspirated into the fourth syringe cylinder through the second hollow needle.

After the plasma fraction has been aspirated, the second hollow needle along with the fourth syringe or the second hollow needle along with the extension tube is pulled out of the third syringe cylinder. The second hollow needle is removed from the fourth syringe cylinder, and then the fourth port is sealed with the fourth cap. Thereby, the plasma fraction is hermetically sealed in the fourth syringe cylinder. Then the fourth plunger is removed from the fourth gasket. The fourth syringe cylinder is centrifuged in this state. By the centrifugation, the plasma fraction is separated into an upper portion (fourth gasket side) substantially consisting only of the supernatant, that is, the plasma component, and a lower portion (fourth-port side) containing platelet-rich plasma containing a large number of platelets. The fourth cap is removed from the fourth syringe cylinder, the fourth plunger is mounted on the fourth gasket, and then the platelet-rich plasma is discharged from the fourth port of the fourth syringe cylinder.

(6) Said second split plunger is preferably detachable from said first split plunger in a threaded fashion. Said fourth plunger is preferably detachable from said fourth gasket in a threaded fashion. Thereby, the second split plunger detachable from the first split plunger and the fourth plunger detachable from the fourth gasket are realized in a simple manner. The second split plunger can be repeatedly attached/detached to/from the first split plunger, and the fourth plunger can be repeatedly attached/detached to/from the fourth gasket.

(7) Said first split plunger preferably has a plug which seals said insertion hole and through which said second hollow needle can be passed. Thereby, even after the second split plunger is removed, the insertion hole of the first split plunger can remain sealed, so that the hermetically sealed state of the third syringe cylinder can be maintained.

(8) Said third syringe and said fourth syringe are preferably provided in a hermetically sealed sterilized package. Provision of these as a kit hermetically sealed in a sterilized package would improve user-friendliness.

(9) A platelet-rich plasma separation method according to the invention uses a first syringe comprising a first syringe cylinder having a first port, a first gasket for sealing the first syringe cylinder liquid-tightly, which first gasket is reciprocated within the first syringe cylinder, and a first plunger provided on the first gasket; and a second syringe comprising a first hollow needle, a second syringe cylinder having a second port on which the first hollow needle can be mounted, a second gasket for sealing the second syringe cylinder liquid-tightly, which second gasket is reciprocated within the second syringe cylinder, and a second plunger provided on the second gasket. The platelet-rich plasma separation method includes a first step of sealing the first port of said first syringe cylinder filled with collected blood; a second step of centrifuging the blood in said first syringe cylinder into a first section containing red blood cells and a second section containing platelets and plasma, with the first-port side of said first syringe cylinder set as the direction of centrifugal movement; a third step of passing the first hollow needle through the first gasket in said first syringe cylinder to aspirate said second section into said second syringe cylinder; a fourth step of sealing the second port of said second syringe cylinder filled with said second section; a fifth step of centrifuging the second section in said second syringe cylinder, with the second-port side of said second syringe cylinder set as the direction of centrifugal movement; and a sixth step of moving the second gasket in said second syringe cylinder to discharge the platelet-rich plasma out of said centrifuged second section through said second port.

The first syringe is used for blood collection. A blood collection needle can be mounted on the first port of the first syringe cylinder. The blood collection needle may be directly mounted on the first port or be mounted on the first port via other members, such as an extension tube. Blood collection is performed by a usual method using the first syringe with a blood collection needle mounted on. The first syringe cylinder is filled with blood (whole blood) through the blood collection. In the first step, the first port of the first syringe is sealed so that the first syringe cylinder is kept in a hermetically sealed state. That is, after blood has been collected, the blood collection needle is removed from the first syringe cylinder. Then the first port of the first syringe cylinder is sealed with a cap.

In the second step, the first centrifugation is performed using the first syringe hermetically sealed. In this centrifugation, the first-port side of the first syringe cylinder is set as the direction of centrifugal movement. Here, the "direction of centrifugal movement" is the direction to which centrifugal force is applied during the centrifugation and, in general, downward. By this centrifugation, the blood hermetically sealed in the first syringe cylinder is separated into a first section and a second section. The first section is a fraction containing red blood cells. The second section contains platelets and plasma. The first section is separated toward the direction of centrifugal movement, that is, downward, by centrifugation.

In the third step, the second section in the first syringe cylinder is aspirated into the second syringe cylinder. After the centrifugation, the second syringe is advanced into the first syringe cylinder. Then the first hollow needle mounted on the second port of the second syringe is passed through the first gasket. It should be noted that the first hollow needle may be directly mounted on the second port or be mounted on the second port via other members, such as an extension tube. When the first hollow needle is mounted on the second port via an extension tube, for example, the first hollow needle and the extension tube are advanced into the first syringe cylinder, and then the first hollow needle is passed through the first gasket. In that state, the second plunger is pulled outwardly from the second syringe cylinder to aspirate the second section in the first syringe cylinder into the second syringe cylinder.

In the fourth step, the second port of the second syringe cylinder filled with the second section is sealed so that the second syringe cylinder is kept in a hermetically sealed state. The second syringe cylinder is filled only with the second section. The second port of the second syringe cylinder is sealed with a cap.

In the fifth step, the second centrifugation is performed using the second syringe hermetically sealed. In this centrifugation, the second-port side of the second syringe cylinder is set as the direction of centrifugal movement. By this centrifugation, the second section is centrifuged, and the platelets are moved in the direction of centrifugal movement, that is, downward.

In the sixth step, the platelet-rich plasma is discharged from the second syringe cylinder. After the centrifugation, the cap is removed from the second syringe cylinder to open the second port. In this state, the second plunger is operated to move the second gasket toward the second-port side. By the second centrifugation, the platelets in the second section are centrifugally moved, whereby the second section is separated into an upper portion substantially consisting only of the supernatant, that is, the plasma component, and a lower portion (second-port side) containing platelet-rich plasma containing a large number of platelets. Accordingly, the platelet-rich plasma is discharged from the second port with the movement of the second gasket. Thereby the platelet-rich plasma is separated from the collected blood.

(10) In said sixth step, it is conceivable to discharge out a predetermined amount of said centrifuged second section as the platelet-rich plasma which is present on said second port side.

(11) It is conceivable that the centrifugation in said second step is weak centrifugation and the centrifugation in said fifth step is strong centrifugation.

By employing weak centrifugation in the second step, the blood (whole blood) can be separated into the first section and the second section. Since platelets fail to concentrate near the boundary between the first section and the second section, the loss of the platelets at the time of the suction of the second section can be reduced. By employing strong centrifugation in the fifth step, high-concentration platelet-rich plasma can be separated from the second section.

(12) The invention can be viewed as the platelet-rich plasma obtained by said platelet-rich plasma separation method.

(13) A platelet-rich plasma separation method according to the invention uses a third syringe comprising a third syringe cylinder having a third port, a third gasket for sealing the third syringe cylinder liquid-tightly, which third gasket is reciprocated within the third syringe cylinder, and a third plunger provided on the third gasket; and a fourth syringe comprising a second hollow needle, a fourth syringe cylinder having a fourth port on which the second hollow needle can be mounted, a fourth gasket for sealing the fourth syringe cylinder liquid-tightly, which fourth gasket is reciprocated within the fourth syringe cylinder, and a fourth plunger provided on the fourth gasket. The platelet-rich plasma separation method includes a seventh step of sealing the third port of said third syringe cylinder filled with collected blood; an eighth step of centrifuging the blood in said third syringe cylinder into a first section containing red blood cells and a second section containing platelets and plasma, with the third-port side of said third syringe cylinder set as the direction of centrifugal movement; a ninth step of passing the second hollow needle through the third gasket in said third syringe cylinder to aspirate said second section into said fourth syringe cylinder; a tenth step of sealing the fourth port of said fourth syringe cylinder filled with said second section; an eleventh step of centrifuging the second section in said fourth syringe cylinder, with the fourth-port side of said fourth syringe cylinder set as the direction of centrifugal movement; and a twelfth step of moving the fourth gasket in said fourth syringe cylinder to discharge the platelet-rich plasma out of said centrifuged second section through said fourth port.

The third syringe is used for blood collection. A blood collection needle can be mounted on the third port of the third syringe cylinder. The blood collection needle may be directly mounted on the third port or be mounted on the third port via other members, such as an extension tube. Blood collection is performed by a usual method using the third syringe with a blood collection needle mounted on. The third syringe cylinder is filled with blood (whole blood) through the blood collection. In the seventh step, the third port of the third syringe is sealed so that the third syringe cylinder is kept in a hermetically sealed state. That is, after blood has been collected, the blood collection needle is removed from the third syringe cylinder. Then the third port of the third syringe cylinder is sealed with a cap.

In the eighth step, the first centrifugation is performed using the third syringe hermetically sealed. In this centrifugation, the third-port side of the third syringe cylinder is set as the direction of centrifugal movement. Here, the "direction of centrifugal movement" is the direction to which centrifugal force is applied during the centrifugation and, in general, downward. By this centrifugation, the blood hermetically sealed in the third syringe cylinder is separated into a first section and a second section. The first section contains red blood cells. The second section contains platelets and plasma. The first section is separated toward the direction of centrifugal movement, that is, downward, by centrifugation.

In the ninth step, the second section in the third syringe cylinder is aspirated into the fourth syringe cylinder. After the centrifugation, the fourth syringe is advanced into the third syringe cylinder. Then the second hollow needle mounted on the fourth port of the fourth syringe is passed through the third gasket. It should be noted that the second hollow needle may be directly mounted on the fourth port or be mounted on the fourth port via other members, such as an extension tube. When the second hollow needle is mounted on the fourth port via an extension tube, for example, the second hollow needle and the extension tube are advanced into the third syringe cylinder, and then the second hollow needle is passed through the third gasket. In that state, the fourth plunger is pulled outwardly from the fourth syringe cylinder to aspirate the second section in the third syringe cylinder into the fourth syringe cylinder.

In the tenth step, the fourth port of the fourth syringe cylinder filled with the second section is sealed so that the fourth syringe cylinder is kept in a hermetically sealed state. The fourth syringe cylinder is filled only with the second section. The fourth port of the fourth syringe cylinder is sealed with a cap.

In the eleventh step, the second centrifugation is performed using the fourth syringe hermetically sealed. In this centrifugation, the fourth-port side of the fourth syringe cylinder is set as the direction of centrifugal movement. By this centrifugation, the second section is centrifuged, and the platelets are moved in the direction of centrifugal movement, that is, downward.

In the twelfth step, the platelet-rich plasma is discharged from the fourth syringe cylinder. After the centrifugation, the cap is removed from the fourth syringe cylinder to open the fourth port. In this state, the fourth plunger is operated to move the fourth gasket toward the fourth port side. By the second centrifugation, the platelets in the second section are centrifugally moved, whereby the second section is separated into an upper portion substantially consisting only of the supernatant, that is, the plasma component, and a lower portion (fourth-port side) containing platelet-rich plasma containing a large number of platelets. Accordingly, the platelet-rich plasma is discharged from the fourth port with the movement of the fourth gasket. Thereby the platelet-rich plasma is separated from the collected blood.

(14) In said twelfth step, it is conceivable to discharge out a predetermined amount of said centrifuged second section as the platelet-rich plasma which is present on said fourth port side.

(15) It is conceivable that the centrifugation in said eighth step is weak centrifugation and the centrifugation in said eleventh step is strong centrifugation.

(16) The invention can be viewed as the platelet-rich plasma obtained by said platelet-rich plasma separation method.

According to the platelet-rich plasma separator and the platelet-rich plasma separation method according to the present invention, platelet-rich plasma can be obtained by centrifuging the syringe used for blood collection. Thereby separation of platelet-rich plasma can be realized using a small number of gamma radiation sterilized instruments. Moreover, by using two syringes, the first section and the second section can be reliably separated, whereby high-concentration platelet-rich plasma can be obtained.

REFERENCE NUMERALS

10—First syringe
11—Second syringe
12—First port
13—First syringe cylinder
14—First cap
15—First gasket
16—First plunger
30—First hollow needle
31—Second port
32—Second syringe cylinder
33—Second cap
34—Second gasket
35—Second plunger
43—Guide piece
48—Mounting hole (guide hole)
60—Third syringe
61—Fourth syringe
62—Third port
63—Third syringe cylinder
64—Third cap
65—Third gasket
66—First split plunger
67—Second split plunger
80—Hole (insertion hole)
83—Plug
90—Second hollow needle
91—Fourth port
92—Fourth syringe cylinder
93—Fourth cap
94—Fourth gasket
95—Fourth plunger

DESCRIPTION OF THE PREFERRED EMBODIMENTS

Preferable embodiments of the present invention will now be described. It should be noted that the embodiments are merely exemplary of the aspects of the present invention and may be modified as appropriate without departing from the spirit or scope of the invention.

[First Embodiment]

Figure 1:
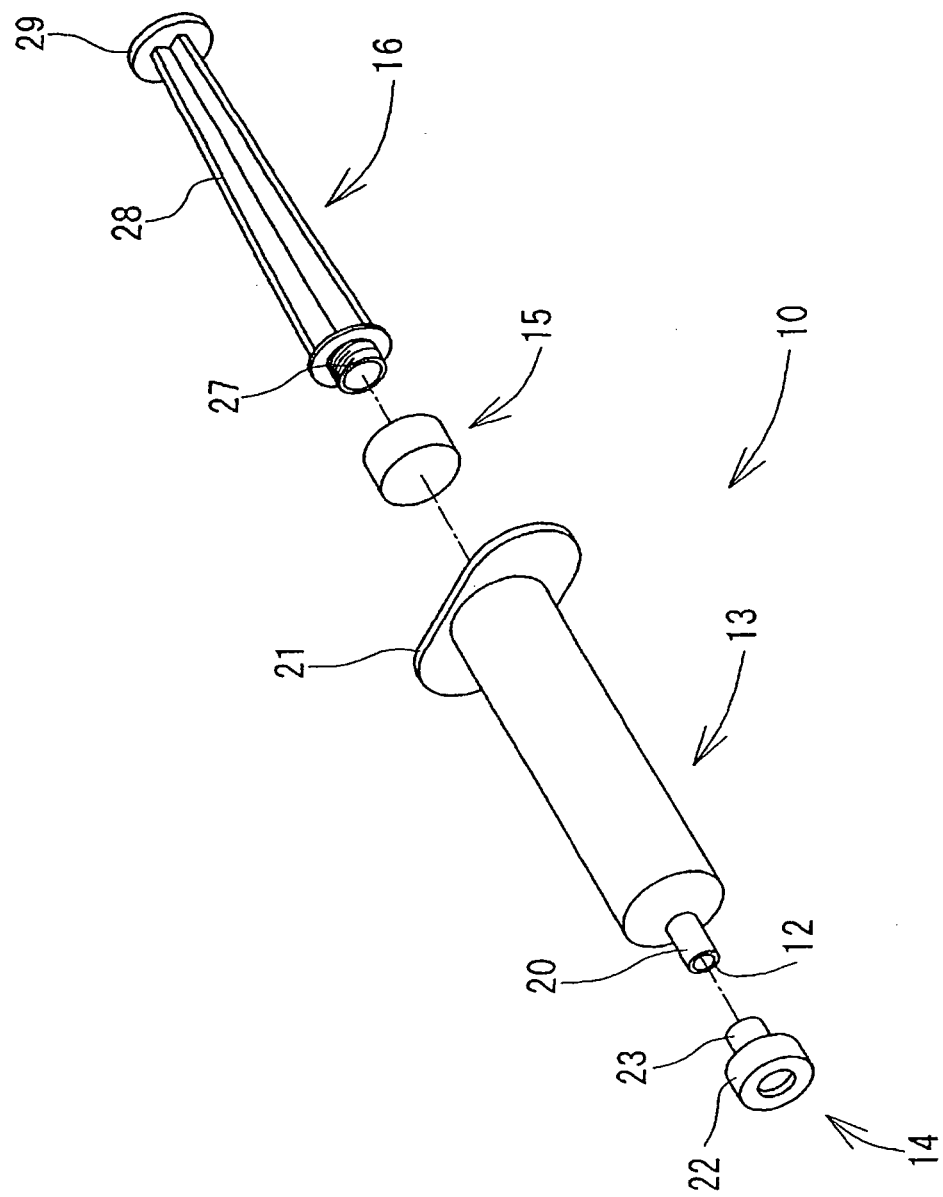
FIG. 1 is an exploded perspective view showing the external configuration of the first syringe 10 of the platelet-rich plasma separator according to the first embodiment of the invention.
Figure 2:
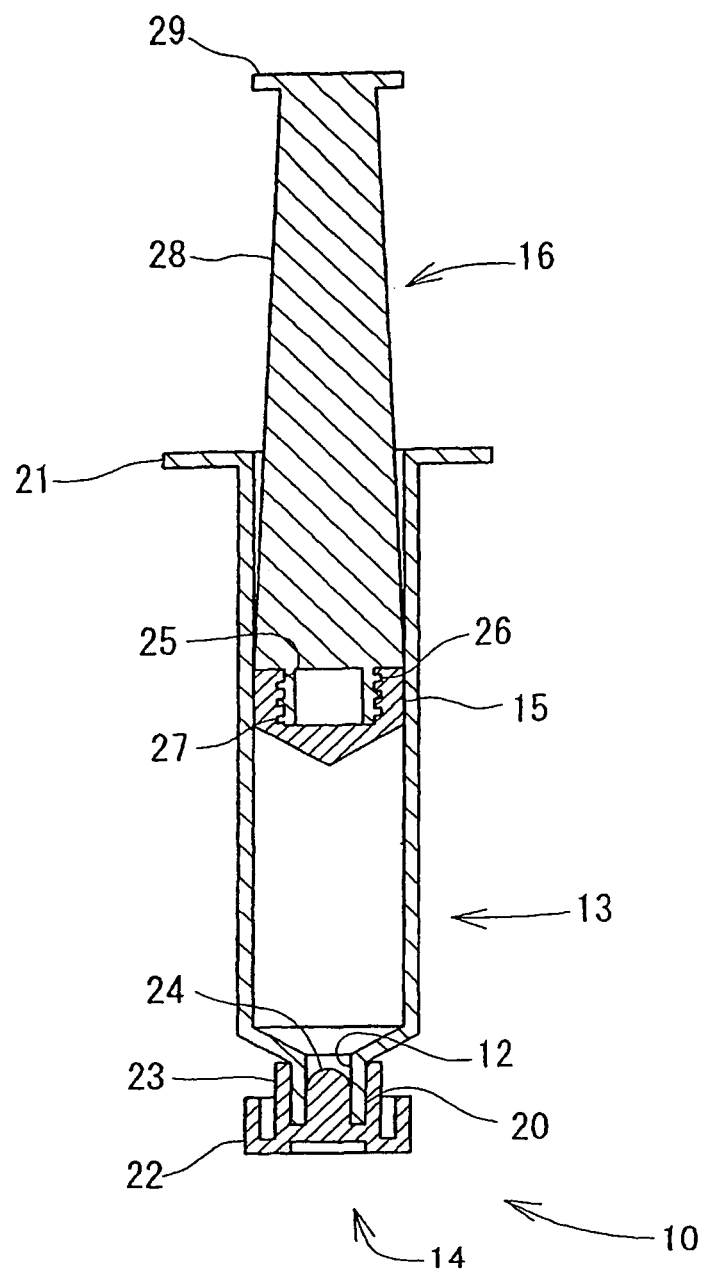
FIG. 2 is a longitudinal sectional view showing the internal configuration of the first syringe 10.
Figure 3:
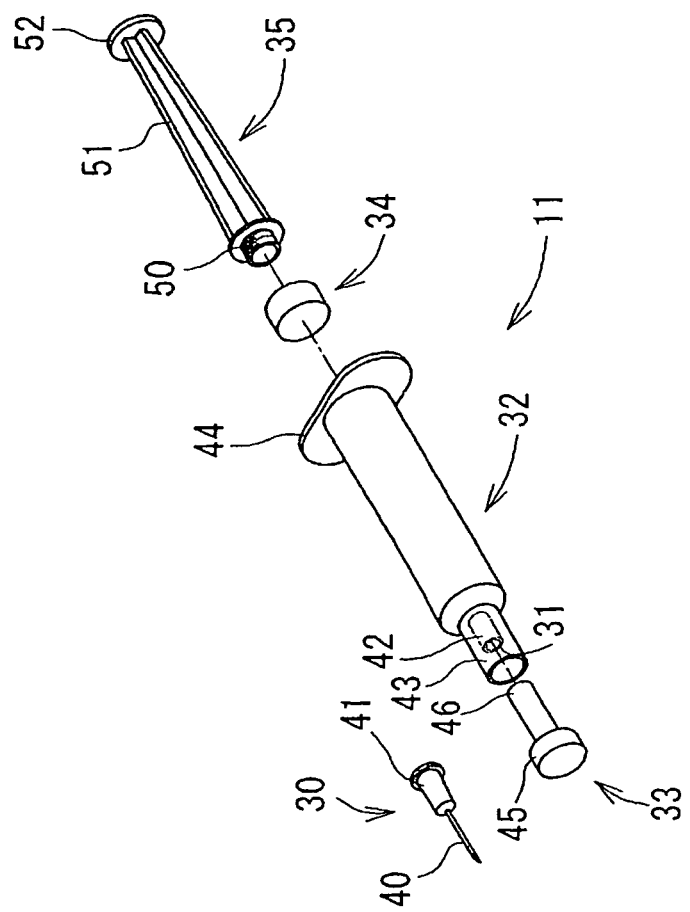
FIG. 3 is an exploded perspective view showing the external configuration of the second syringe 11 of the platelet-rich plasma separator according to the first embodiment of the invention.
Figure 4:
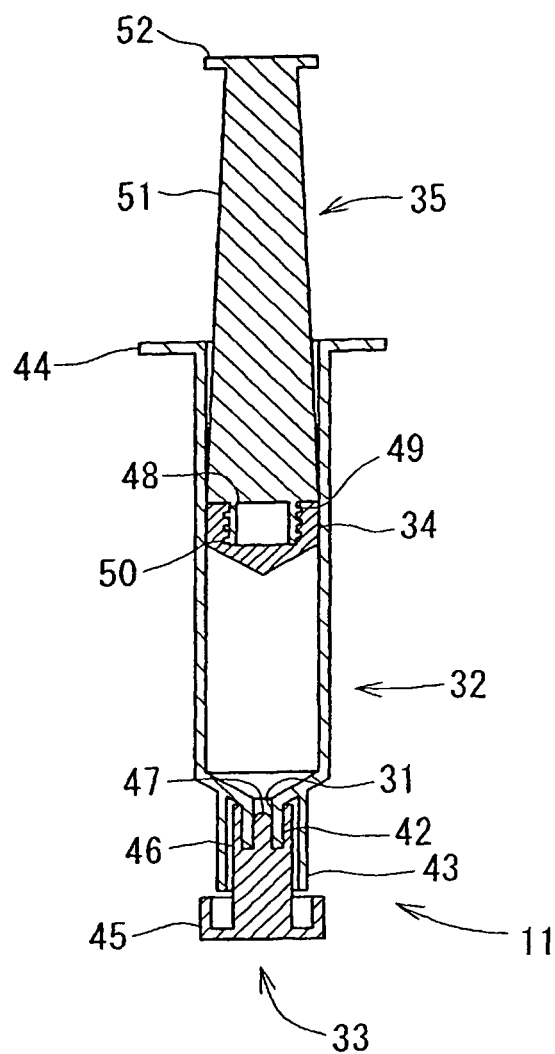
FIG. 4 is a longitudinal sectional view showing the internal configuration of the second syringe 11.

FIG. 1 is an exploded perspective view showing the external configuration of the first syringe 10 of the platelet-rich plasma separator according to the first embodiment of the invention. FIG. 2 is a longitudinal sectional view showing the internal configuration of the first syringe 10. FIG. 3 is an exploded perspective view showing the external configuration of the second syringe 11 of the platelet-rich plasma separator according to the first embodiment of the invention. FIG. 4 is a longitudinal sectional view showing the internal configuration of the second syringe 11.

The platelet-rich plasma separator according to the present invention comprises a first syringe 10 and a second syringe 11. The first syringe 10 is used in order to aspirate blood. Suction of blood is exemplified, in particular, by blood collection but not limited thereto, and includes the suction of the blood which has already been collected. The second syringe 11 is used in order to aspirate the fraction containing white blood cells, platelets, and plasma (corresponding to the second section of the present invention), the fraction having been formed in the first syringe 10 by centrifugation.

As shown in FIG. 1 and FIG. 2, the first syringe 10 comprises a first syringe cylinder 13 having a first port 12 on which a blood collection needle can be mounted, a first cap 14 detachable from the first port 12, a first gasket 15 reciprocated within the first syringe cylinder 13, and a first plunger 16 provided detachably on the first gasket 15.

The first syringe cylinder 13 has a substantially cylindrical shape, one end portion thereof having a reduced diameter to form a needle mount 20. The internal space of the needle mount 20 communicates with the internal space of the first syringe cylinder 13. By means of the needle mount 20, the first port 12 according to the present invention is formed. A blood collection needle can be mounted on the needle mount 20. The other end portion of the first syringe cylinder 13 is open without having a reduced diameter. From the other end, the first plunger 16 is moved into and out of the internal space of the first syringe cylinder 13. At the other end portion of the first syringe cylinder 13, a flange 21 projecting in the peripheral direction of the first syringe cylinder 13 is formed. The flange 21 is provided for better handling, and fingers are put on the flange 21 in operating the first syringe cylinder 13 and the first plunger 16.

The material of the first syringe cylinder 13 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, it is common to use a molded article of polypropylene as the first syringe cylinder 13. In order to perform visual check of blood, plasma, etc. filled in the internal space of the first syringe cylinder 13, the first syringe cylinder 13 is preferably transparent or translucent. The volume of the first syringe cylinder 13 is not limited in particular. The first syringe cylinder 13 is preferably graduated so that the quantity etc. of the liquid filled in the internal space thereof can be easily known.

The first cap 14 seals the first port 12 of the first syringe cylinder 13. As shown in FIG. 1 and FIG. 2, the first cap 14 has a major diameter part 22 and a narrow diameter part 23. The narrow diameter part 23 is arranged in the space inside the major diameter part 22. The narrow diameter part 23 has a tubular shape which can be fitted onto the needle mount 20 of the first syringe cylinder 13. A plug part 24 which can be fitted in the first port 12 of the first syringe cylinder 13 is arranged in the interior of the narrow diameter part 23. The major diameter part 22 serves as a grip to be used in attaching/ detaching the first cap 14 to/from the first syringe cylinder 13. Once the first cap 14 is mounted on the first syringe cylinder 13, the narrow diameter part 23 tightly fits to the outer periphery of the needle mount 20, the plug part 24 fits in the first port 12, and thus the first port 12 is sealed liquid-tightly as shown in FIG. 2.

The material of the first cap 14 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, a molded article of polypropylene or elastomer can be used as the first cap 14.

The first gasket 15 is inserted within the interior of the first syringe cylinder 13 to seal the first syringe cylinder 13 liquid-tightly. The first gasket 15 can be reciprocated within the first syringe cylinder 13 in a liquid tight manner. Reciprocation of the first gasket 15 causes a change of the volume of the liquid which can be hermetically sealed within the first syringe cylinder 13. As shown in FIG. 1, the first gasket 15 has a cylindrical shape with a diameter corresponding to the internal diameter of the first syringe cylinder 13. As shown in FIG. 2, one end face of the first gasket 15 is projected in a conical shape. The shape of this face corresponds to the shape of the innermost end of the first syringe cylinder 13. A mounting hole 25 is formed in the other end face of the first gasket 15, the side to be connected to the first plunger 16. The mounting hole 25 is formed in the center of the circular end face of the first gasket 15. The mounting hole 25 is a circular hole. The mounting hole 25 corresponds to the guide hole according to the present invention. A female screw 26 is formed in the inner periphery of the mounting hole 25.

The material of the first gasket 15 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, a molded article of elastomer can be used as the first gasket 15.

The first plunger 16 is detachable from the first gasket 15 in a threaded fashion. For the overall configuration, the first plunger 16 has the contour that can be inserted in the internal space of the first syringe cylinder 13 and is sufficiently longer than the axial (the direction of the dotted and dashed line in FIG. 1; the vertical direction in FIG. 2) length of the first syringe cylinder 13. Accordingly, with the first gasket 15 pushed up to the innermost end (first-port 12 side) of the first syringe cylinder 13, a portion of the first plunger 16 is projected from the opposite end of the first syringe cylinder 13.

The first plunger 16 has a male screw part 27, an shaft part 28, and an end plate 29. The male screw part 27 is threaded into the mounting hole 25 of the first gasket 15. The female screw 26 of the mounting hole 25 engages the male screw part 27. Thereby the first plunger 16 is attached/detached to/from the first gasket 15 in a threaded fashion. This attachment and detachment can be performed repeatedly.

The shaft part 28 has a cross-shaped cross section (direction perpendicular to the axial direction). The cross-sectional shape of the shaft part 28 can be suitably selected in consideration of easiness of molding, strength, etc. The male screw part 27 is arranged at one end of the shaft part 28, and the end plate 29 is arranged at the other end. The end plate 29 is a disc-shaped flat plate and is connected to the shaft part 28 perpendicular to the axial direction of the shaft part 28. The end plate 29, provided for better handling of the first plunger 16, is pressed by a finger when the first plunger 16 is pushed into the first syringe cylinder 13, and serves as a grip when the first plunger 16 is pulled outwardly from the first syringe cylinder 13.

The material of the first plunger 16 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, it is common to use a molded article of polypropylene as the first plunger 16.

As shown in FIG. 3 and FIG. 4, the second syringe 11 comprises a first hollow needle 30, a second syringe cylinder 32 having a second port 31 on which the first hollow needle 30 can be mounted, a second cap 33 detachable from said second port 31, a second gasket 34 reciprocated within the second syringe cylinder 32, and a second plunger 35 provided detachably on the second gasket 34.

The first hollow needle 30 has a canula 40 with a blade face formed at the tip of the hollow tube, and a hub 41 connected to the proximal end of the canula 40. The axial length of the canula 40 is set to be the length necessary for the canula 40 to be passed through the first gasket 15 of the first syringe 10. The hub 41 has a substantially cylindrical shape and is set to have an internal diameter and an axial length necessary to be fitted onto the needle mount 42 of the second syringe cylinder 32. The end portion of the hub 41 to which the proximal end of the canula 40 is connected is closed except the portion that is connected to the canula 40. The canula 40 and the hub 41 are fixed together by means of adhesives etc. The end portion of the hub 41 which is to be connected to the needle mount 42 is open. The opening at the proximal end of the canula 40 communicates with the internal space of the hub 41. Accordingly, the liquid etc. entering the opening at the tip of the canula 40 and advancing through the canula 40 flows through the opening at the proximal end of the canula 40 into the internal space of the hub 41. This internal space communicates with the second port 31 by the hub 41 being fitted onto the needle mount 42.

The second syringe cylinder 32 has a substantially cylindrical shape and is of a size that can be advanced into the internal space of first syringe cylinder 13. One end portion of the second syringe cylinder 32 has a reduced diameter to form a needle mount 42. The internal space of the needle mount 42 communicates with the internal space of the second syringe cylinder 32. By means of the needle mount 42, the second port 31 according to the present invention is formed. A first hollow needle 30 can be mounted on the needle mount 42. A guide piece 43 is formed on the second syringe cylinder 32 around the needle mount 42. The guide piece 43 has a cylindrical shape, one end thereof being connected to the second syringe 32, the other end being open in the same direction as the second port 31. A gap is formed between the inner surface of the guide piece 43 and the outer surface of the needle mount 42. This gap is set to have an appropriate size so that the hub 41 of the first hollow needle 30 or the narrow diameter part 46 of the second cap 33 can be inserted therein, respectively. The axial length of the guide piece 43 is set to be sufficiently longer than the axial length of the needle mount 42, and in particular, long enough to completely cover the hub 41 of the first hollow needle 30 mounted on the needle mount 42. The external diameter of the guide piece 43 corresponds to the internal diameter of the mounting hole 25 of the first gasket 15, and the guide piece 43 can be fitted in the mounting hole 25. It should be noted that although the guide piece 43 is integrally formed with the second syringe cylinder 32 in this embodiment, the guide piece 43 may be detachable from the second syringe cylinder 32 for easier mounting of the first hollow needle 30 onto the needle mount 42.

The other end portion of the second syringe cylinder 32 is open without having a reduced diameter. From the other end, the second plunger 35 is moved into and out of the internal space of the second syringe cylinder 32. At the other end portion of the second syringe cylinder 32, a flange 44 projecting in the peripheral direction of the second syringe cylinder 32 is formed. The flange 44 is provided for better handling, and fingers are put on the flange 44 in operating the second syringe cylinder 32 and the second plunger 35.

The material of the second syringe cylinder 32 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, it is common to use a molded article of polypropylene as the second syringe cylinder 32. In order to perform visual check of plasma, etc. filled in the internal space of the second syringe cylinder 32, the second syringe cylinder 32 is preferably transparent or translucent. The volume of the second syringe cylinder 32 is not limited in particular. The second syringe cylinder 32 is preferably graduated so that the quantity etc. of the liquid filled in the internal space thereof can be easily known.

The second cap 33 seals the second port 31 of the second syringe cylinder 32. As shown in FIG. 3 and FIG. 4, the second cap 33 has a major diameter part 45 and a narrow diameter part 46. The narrow diameter part 46 is arranged in the space inside the major diameter part 45. The narrow diameter part 46 has a tubular shape which can be fitted onto the needle mount 42 of the second syringe cylinder 32. The axial length of the narrow diameter part 46 is sufficiently longer than the axial length of the guide piece 43, whereby with the second cap 33 mounted on the needle mount 42, the major diameter part 45 and the guide piece 43 do not interfere with each other. A plug part 47 which can be fitted in the second port 31 of the second syringe cylinder 32 is arranged in the interior of the narrow diameter part 46. The major diameter part 45 serves as a grip to be used in attaching/detaching the second cap 33 to/from the second syringe cylinder 32. Once the second cap 33 is mounted on the second syringe cylinder 32, the narrow diameter part 46 tightly fits to the outer periphery of the needle mount 42, the plug part 47 fits in the second port 31, and thus the second port 31 is sealed liquid-tightly as shown in FIG. 4.

The material of the second cap 33 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, a molded article of polypropylene or elastomer can be used as the second cap 33.

The second gasket 34 is inserted within the interior of the second syringe cylinder 32 to seal the second syringe cylinder 32 liquid-tightly. The second gasket 34 can be reciprocated within the second syringe cylinder 32 in a liquid tight manner. Reciprocation of the second gasket 34 causes a change of the volume of the liquid which can be hermetically sealed within the second syringe cylinder 32. As shown in FIG. 3, the second gasket 34 has a cylindrical shape with a diameter corresponding to the internal diameter of the second syringe cylinder 32. As shown in FIG. 4, one end face of the second gasket 34 is projected in a conical shape. The shape of this face corresponds to the shape of the innermost end of the second syringe cylinder 32. A mounting hole 48 is formed in the other end face of the second gasket 34, the side to be connected to the second plunger 35. The mounting hole 48 is formed in the center of the circular end face of the second gasket 34. The mounting hole 48 is a circular hole. A female screw 49 is formed in the inner periphery of the mounting hole 48.

The material of the second gasket 34 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, a molded article of elastomer can be used as the second gasket 34.

The second plunger 35 is detachable from the second gasket 34 in a threaded fashion. For the overall configuration, the second plunger 35 has the contour that can be inserted in the internal space of the second syringe cylinder 32 and is sufficiently longer than the axial (the direction of the dotted and dashed line in FIG. 3; the vertical direction in FIG. 4) length of the second syringe cylinder 32. Accordingly, with the second gasket 34 pushed up to the innermost end (second-port 31 side) of the second syringe cylinder 32, a portion of the second plunger 35 is projected from the opposite end of the second syringe cylinder 32.

The second plunger 35 has a male screw part 50, an shaft part 51, and an end plate 52. The male screw part 50 is threaded into the mounting hole 48 of the second gasket 34. The female screw 49 of the mounting hole 48 engages the male screw part 50. Thereby the second plunger 35 is attached/detached to/from the second gasket 34 in a threaded fashion. This attachment and detachment can be performed repeatedly.

The shaft part 51 has a cross-shaped cross section (direction perpendicular to the axial direction). The cross-sectional shape of the shaft part 51 can be suitably selected in consideration of easiness of molding, strength, etc. The male screw part 50 is arranged at one end of the shaft part 51, and the end plate 52 is arranged at the other end. The end plate 52 is a disc-shaped flat plate and is connected to the shaft part 51 perpendicular to the axial direction of the shaft part 51. The end plate 52, provided for better handling of the second plunger 35, is pressed by a finger when the second plunger 35 is pushed into the second syringe cylinder 32, and serves a grip when the second plunger 35 is pulled outwardly from the second syringe cylinder 32.

The material of the second plunger 35 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, it is common to use a molded article of polypropylene as the second plunger 35.

In consideration of obtaining the platelet-rich plasma suitable for regeneration medicine, of the members that form a platelet-rich plasma separator, at least the first syringe cylinder 13, the first cap 14, the first gasket 15, the first hollow needle 30, the second syringe cylinder 32, the second cap 33, and the second gasket 34, which will be in contact with the collected blood, are sterilized by gamma radiation. Provision of the first syringe 10 and the second syringe 11 as a kit hermetically sealed in a sterilized package would improve the user-friendliness of the platelet-rich plasma separator.

The configuration of each member of the first syringe 10 and the second syringe 11 according to this embodiment is merely exemplary, and part of the configuration of each member may be modified to a known configuration without departing from the spirit or scope of the invention. For example, the blood collection needle may be directly or via an extension tube etc. mounted on the needle mount 20 of the first syringe 10. Likewise, for example, the first hollow needle 30 may be directly or via an extension tube etc. mounted on the needle mount 42 of the second syringe 11.

Figure 6:
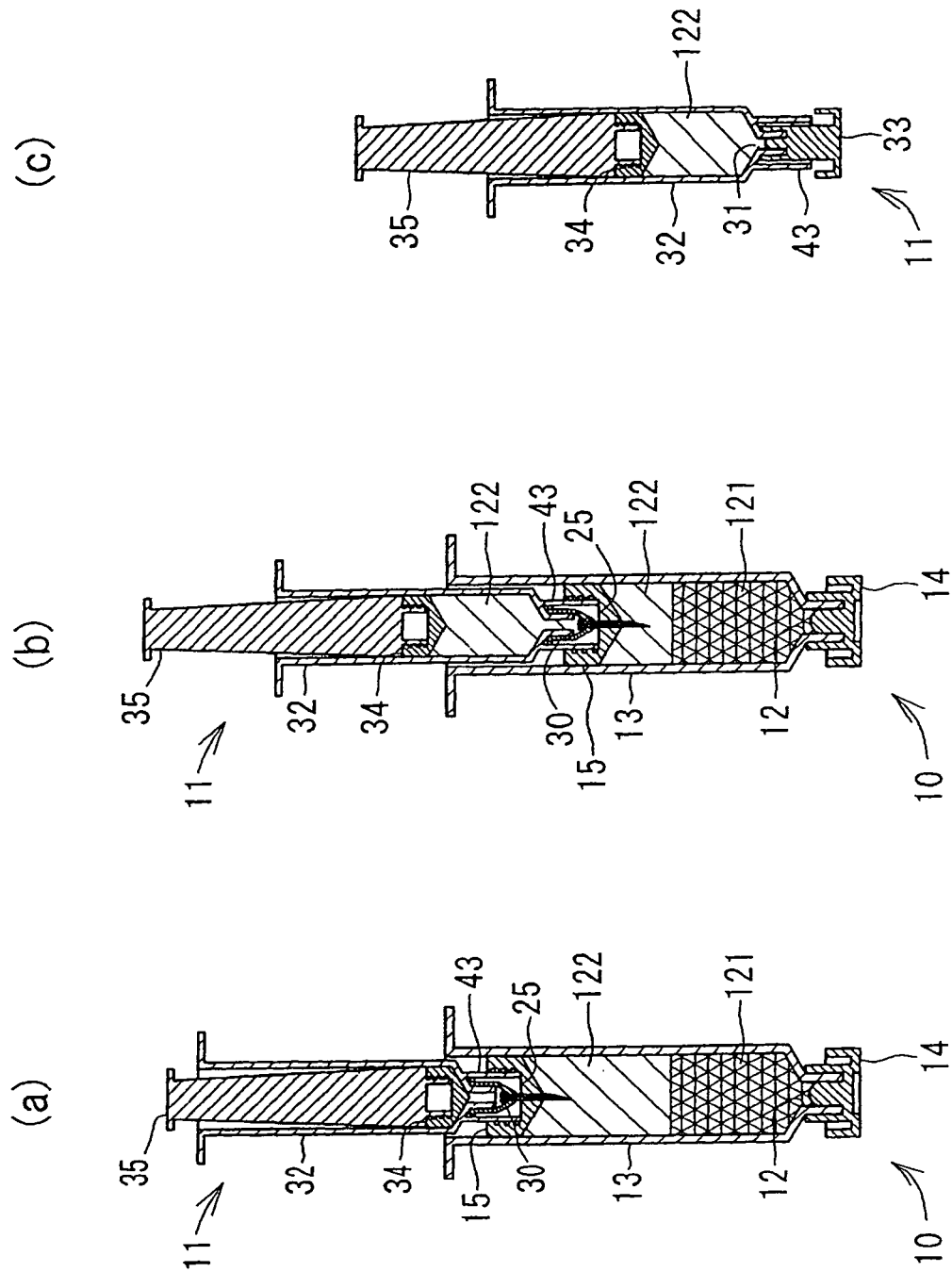
FIG. 6 is a cross-sectional view showing the state of the platelet-rich plasma separator in each step of the platelet-rich plasma separation method according to the first embodiment.
Figure 7:
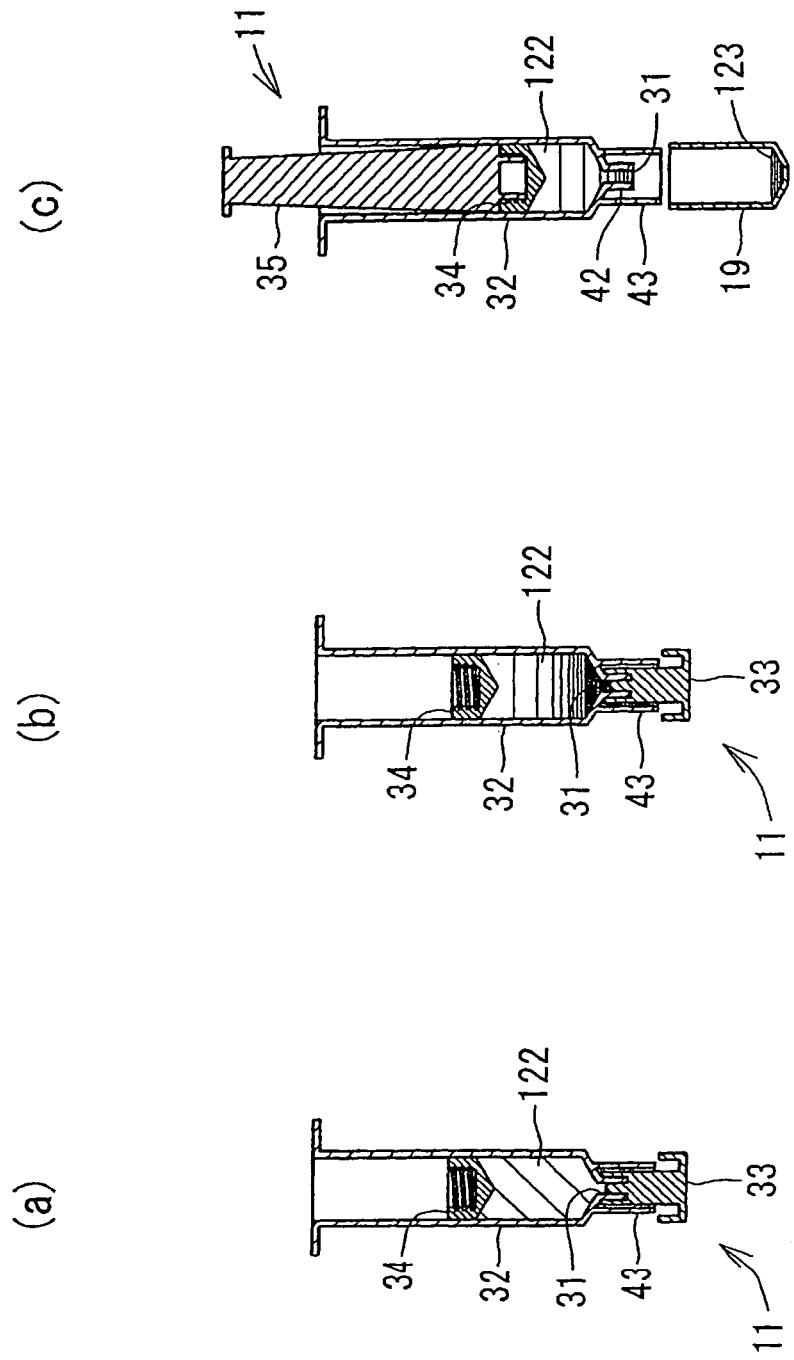
FIG. 7 is a cross-sectional view showing the state of the platelet-rich plasma separator in each step of the platelet-rich plasma separation method according to the first embodiment.

The platelet-rich plasma separation method according to the present invention will now be explained. The platelet-rich plasma separation method according to the embodiment is performed using said platelet-rich plasma separator and consists mainly of six steps. In the first step, the first port 12 of the first syringe cylinder 13 filled with collected blood 120 is sealed. In the second step, the blood 120 in the first syringe cylinder 13 is centrifuged into a first section 121 containing red blood cells and a second section 122 containing white blood cells, platelets and plasma, with the first-port 12 side of the first syringe cylinder 13 set as the direction of centrifugal movement. In the third step, the first hollow needle 30 is passed through the first gasket 15 in the first syringe cylinder 13, to aspirate the second section 122 into the second syringe cylinder 32. In the fourth step, the second port 31 of the second syringe cylinder 32 filled with the second section 122 is sealed. In the fifth step, the second section 122 in the second syringe cylinder 32 is centrifuged, with the second-port 31 side of the second syringe cylinder 32 set as the direction of centrifugal movement. In the sixth step, the second gasket 34 in the second syringe cylinder 32 is moved to discharge the platelet-rich plasma 123 out of the centrifuged second section 122 through the second port 31. These steps will now be explained in detail using FIG. 5 to FIG. 7. Each one of FIG. 5 to FIG. 7 is a cross-sectional view showing the state of the platelet-rich plasma separator in each step of the platelet-rich plasma separation method.

Figure 5:
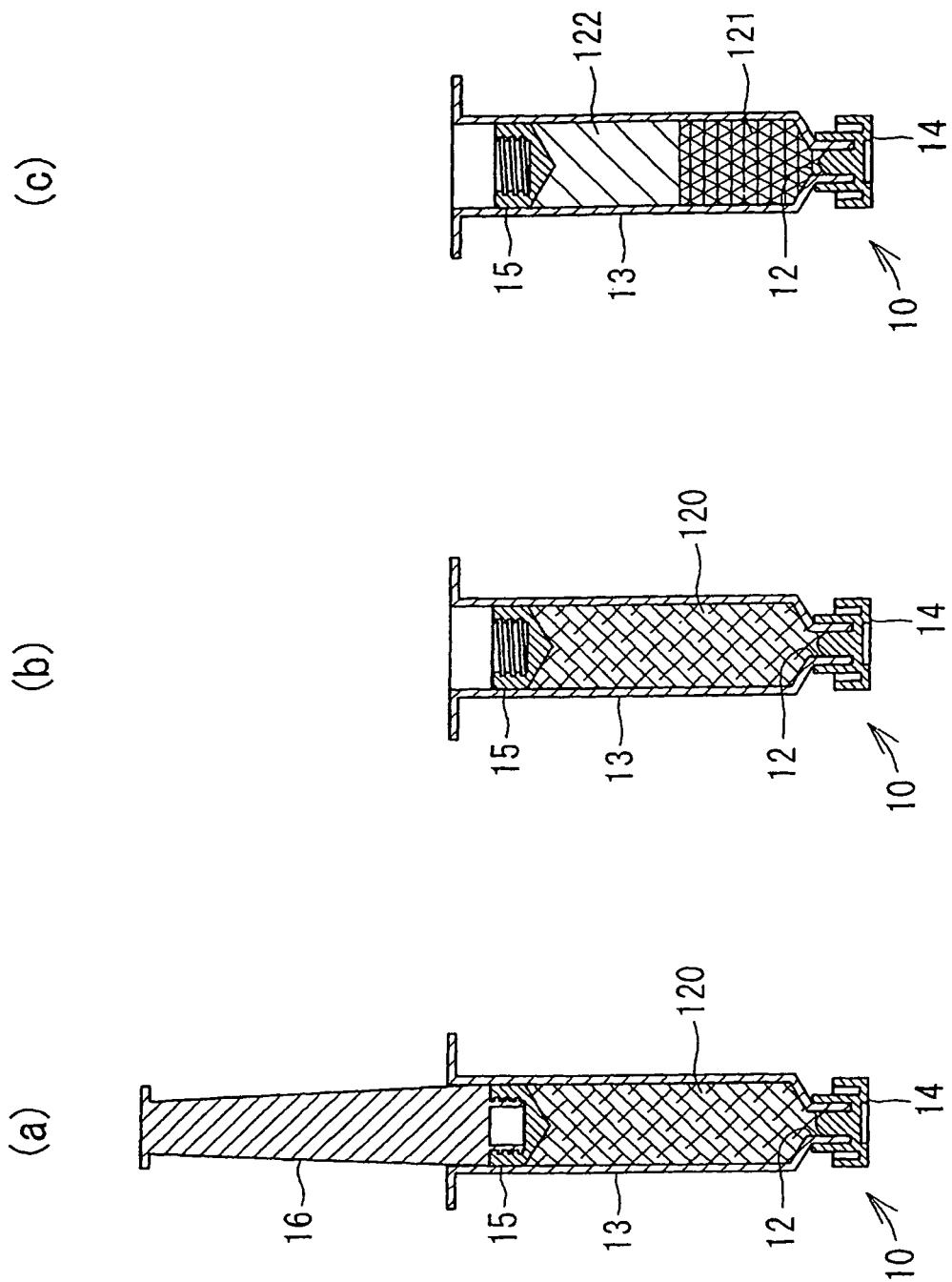
FIG. 5 is a cross-sectional view showing the state of the platelet-rich plasma separator in each step of the platelet-rich plasma separation method according to the first embodiment.

In the first step, the first port 12 of the first syringe cylinder 13 is sealed with the first cap 14 to hermetically seal the first syringe cylinder 13 as shown in FIG. 5 (*a*). The first syringe 10 is used for blood collection. In collecting blood, a blood collection needle is mounted on the first port 12 of the first syringe cylinder 13. Of course, the blood collection needle may be mounted on the first port 12 via an extension tube etc. The first plunger 16 is mounted on the first gasket 15. Blood collection is performed by a usual method, and thus the detailed explanation is omitted. By this blood collection, the first syringe cylinder 13 is filled with blood 120. The blood 120 is whole blood, containing red blood cells, white blood cells, platelets, plasma, etc. After the blood collection, the blood collection needle is removed from the first port 12 of the first syringe cylinder 13, and then the first port 12 is sealed with the first cap 14. Thereby the first syringe cylinder 13 is in a hermetically sealed state as shown in FIG. 5 (*a*).

In the second step, the first centrifugation is performed using the hermetically sealed syringe. Prior to this centrifugation, the first plunger 16 is removed from the first gasket 15 as shown in FIG. 5 (*b*). This prevents the first plunger 16 from being projected from the first syringe cylinder 13, thereby achieving easier handling of the first syringe cylinder 13 at the time of centrifugation. Moreover, the first plunger 16 cannot be operated carelessly during the centrifugation. Further, the weight of the first plunger 16 does not act on the first gasket 15 during the centrifugation, thereby reducing the risk of the first cap 14 coming off the first syringe cylinder 13.

In this centrifugation, the first-port 12 side of the first syringe cylinder 13 is set as the direction of centrifugal movement. Here, the "direction of centrifugal movement" is the direction to which centrifugal force is applied during the centrifugation and, in general, downward. The centrifugation in the second step is weak centrifugation. Weak centrifugation, which is commonly used in the centrifugation of blood, is defined, in general, as "centrifugation that separates whole blood into red blood cells and others (white blood cells, platelets, plasma)" (see Nonpatent Literature 1). Specifically, the centrifugation under the centrifugation condition of approximately 500 to 2500 rpm is considered as weak centrifugation. Since a common type of centrifuge is used here, the detailed description is omitted.

By this centrifugation, the blood 120 hermetically sealed in the first syringe cylinder 13 is separated into a first section 121 and a second section 122. The first section 121 is a fraction containing red blood cells. The second section 122 is a fraction containing white blood cells, platelets, and plasma. As shown in FIG. 5 (*c*), the first section 121 is separated toward the direction of centrifugal movement, that is, toward the lower part of the first syringe cylinder 13, by centrifugation.

In the third step, the second section 122 in the first syringe cylinder 13 is aspirated into the second syringe cylinder 32. After the first centrifugation, the second syringe 11 is advanced into the first syringe cylinder 13 from above as shown in FIG. 6 (*a*). Then, the guide piece 43 of the second syringe cylinder 32 is fitted in the mounting hole 25 of the first gasket 15. Thereby the second syringe cylinder 32 and the first gasket 15 are fitted with each other. Concurrently, the first hollow needle 30 mounted on the second port 31 of the second syringe 32 is passed through the first gasket 15. Thereby the tip of first hollow needle 30 reaches the second section 122 in the first syringe cylinder 13. In that state, the second plunger 35 of the second syringe 11 is pulled outwardly from the second syringe cylinder 32 to aspirate the second section 122 in the first syringe cylinder 13 into the second syringe cylinder 32. It should be noted that when the first hollow needle 30 is mounted on the second port 31 via an extension tube etc., only the first hollow needle 30 and the extension tube can be advanced into the first syringe cylinder 13 so as to pass the first hollow needle 30 through the first gasket 15, instead of advancing the second syringe 11 into the first syringe cylinder 13.

As shown in FIG. 6 (*b*), as the second plunger 35 is pulled outwardly from the second syringe cylinder 32, the second section 122 in the first syringe cylinder 13 is aspirated into the second syringe cylinder 32 and the first gasket 15 is moved within the first syringe cylinder 13 toward the first-port 12 side. Since the first gasket 15 and the second syringe cylinder 32 are fitted with each other, the second syringe cylinder 32 is advanced further into the first syringe cylinder 13 with the movement of the first gasket 15. Thereby the suction of the second section 122 from the first syringe cylinder 13 into the second syringe cylinder 32 is performed smoothly and continuously. Although the first section 121 and small quantities of the second section 122 will remain in the first syringe cylinder 13 at this time, they will be disposed or used for other purposes.

By employing weak centrifugation in the second step, the blood 120 can be separated into the first section 121 and the second section 122, and the platelets can be distributed almost uniformly in the second section 122 as well. That is, the platelets fail to concentrate near the boundary of the first section 121. This can reduce the loss of platelets which would be caused by the slight loss of the second section 122 generated at the time of suction of the second section 122 from the first syringe cylinder 13 into the second syringe cylinder 32.

In the fourth step, the second port 31 of the second syringe 32 is sealed with the second cap 33 so that the second syringe cylinder 32 is kept in a hermetically sealed state. As shown in FIG. 6 (*b*), the second syringe cylinder 32 is filled only with the second section 122 aspirated from the first syringe cylinder 13. When the second syringe 11 is pulled out of the first syringe cylinder 13 with the second plunger 35 fixed, the first gasket 15 in the hermetically sealed first syringe cylinder 13 remains stationary without moving in the first syringe cylinder 13. As a result, the guide piece 43 of the second syringe cylinder 32 comes off the mounting hole 25 of the first gasket 15, disengaging the first gasket 15 from the second syringe cylinder 32. Concurrently, the first hollow needle 30 comes out of the first gasket 15. After the second syringe 11 being completely pulled out of the first syringe cylinder 13, the first hollow needle 30 is removed from the second syringe cylinder 32 to seal the second port 31 with the second cap 33 as shown in FIG. 6 (c). Thereby the second syringe cylinder 32 is hermetically sealed, filled with the second section 122.

In the fifth step, the second centrifugation is performed using the second syringe cylinder 32 hermetically sealed. Prior to this centrifugation, the second plunger 35 is removed from the second gasket 34 as shown in FIG. 7 (a). This prevents the second plunger 35 from being projected from the second syringe cylinder 32, thereby achieving easier handling of the second syringe cylinder 32 at the time of centrifugation. Moreover, the second plunger 35 cannot be operated carelessly during the centrifugation. Further, the weight of the second plunger 35 does not act on the second gasket 34 during the centrifugation, thereby reducing the risk of the second cap 33 coming off the second syringe cylinder 32.

In this centrifugation, the second-port 31 side of the second syringe cylinder 32 is set as the direction of centrifugal movement. The centrifugation in the fifth step is strong centrifugation. Strong centrifugation, which is commonly used in the centrifugation of blood, is defined, in general, as "centrifugation that separates platelets, white blood cells and remaining red blood cells from plasma" (see Nonpatent Literature 1). In the present invention, the centrifugation that condenses platelets in the lower part of the second section is called strong centrifugation. Specifically, the centrifugation under the centrifugation condition of approximately 3000 to 4000 rpm is considered as strong centrifugation. By this centrifugation, the second section 122 is centrifuged, and platelets are moved toward the direction of centrifugal movement, that is, toward the lower part of the second syringe cylinder 32 as shown in FIG. 7 (b). By employing the strong centrifugation, high-concentration PRP 123 can be separated from the second section 122. In FIG. 7 (b), the higher the density of the horizontal lines in the second section 122 is, the higher the platelet concentration is. In fact, in the centrifuged second section 122, that the platelets have moved towards the lower part can be confirmed visually by means of the gradation from substantial transparence to deep yellow formed from the upper part towards the lower part.

In the sixth step, the PRP 123 is discharged from the second syringe cylinder 32. After the completion of the centrifugation, the second plunger 35 is mounted on the second gasket 34 as shown in FIG. 7 (c). Thereby the second gasket 34 can be moved easily. Then the second cap 33 is removed from the second syringe cylinder 32 to open the second port 31. In this state, the second plunger 35 is operated to move the second gasket 34 toward the second-port 31 side. By the second centrifugation, the platelets in the second section 122 has been centrifugally moved, whereby the second section 122 has been separated into an upper portion substantially consisting only of the supernatant, that is, the plasma component, and a lower portion (second-port 31 side) containing the PRP 123 containing a large number of platelets. Accordingly, the PRP 123 is discharged from the second port 31 with the movement of the second gasket 34. The discharged PRP 123 is received in a sterilized container 19. Thereby the PRP 123 is separated from the collected blood 120.

There is not necessarily a clear definition of the platelet concentration in PRP 123. However, suppose, for example, the platelet concentration is expressed in terms of the platelet count in 1 mL, the platelet concentration of the PRP 123 would be 3-7 times higher than that of the collected whole blood. Meanwhile, in the platelet-rich plasma separation method according to the invention, a predetermined amount taken from the second-port 31 side of the second section 122 centrifuged in the sixth step may be defined as the PRP 123. By the platelet-rich plasma separation method according to this embodiment, approximately 1 mL of the PRP 123 can be obtained, for example, from approximately 10 mL of the blood 120.

In this embodiment, the PRP 123 in the sixth step is directly discharged from the second port 31 of the second syringe cylinder 32 into the container 19 etc. However, it should be noted that for prevention of infection, etc., a tube and a three way stopcock, etc. may be connected to the second port 31 of the second syringe cylinder 32 so that the PRP 123 to be discharged can be aspirated in another syringe.

Thus, according to the platelet-rich plasma separator and the platelet-rich plasma separation method according to the invention, PRP 123 can be obtained from the blood 120 by centrifuging the first syringe 10 used for blood collection. Thereby, separation of the PRP 123 can be realized using a small number of gamma radiation sterilized instruments. Moreover, by using two syringes 10,11, the first section 121 and the second section 122 can be reliably separated, whereby high-concentration PRP 123 can be obtained.

[Second Embodiment]

Figure 8:
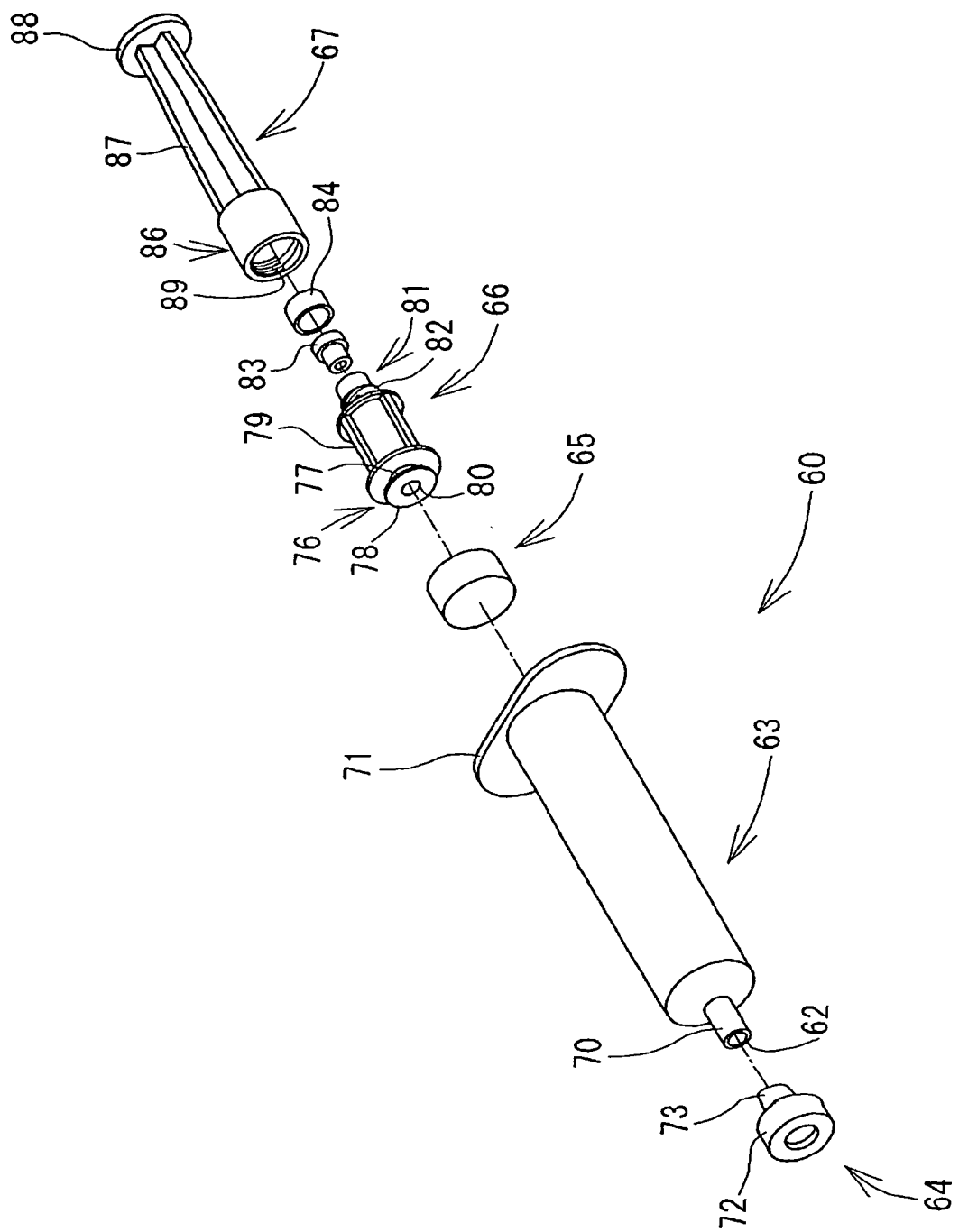
FIG. 8 is an exploded perspective view showing the external configuration of the third syringe 60 of the platelet-rich plasma separator according to the second embodiment of the invention.
Figure 9:
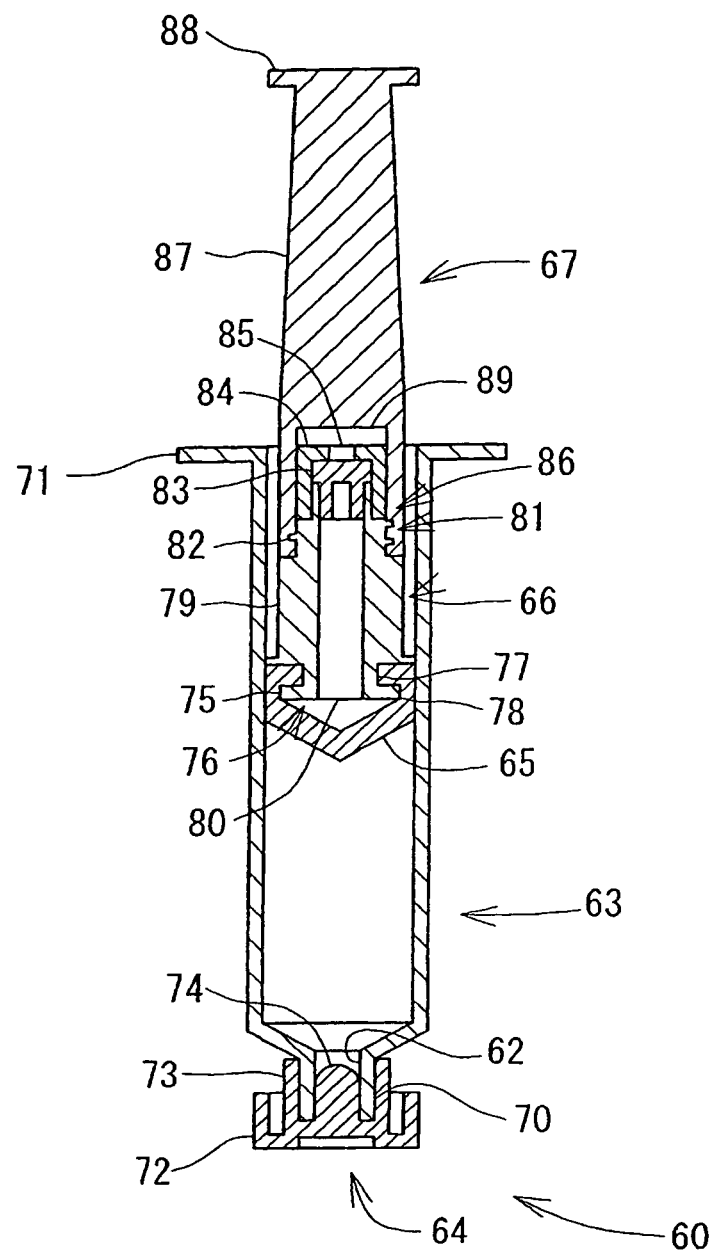
FIG. 9 is a longitudinal sectional view showing the internal configuration of the third syringe 60.
Figure 10:
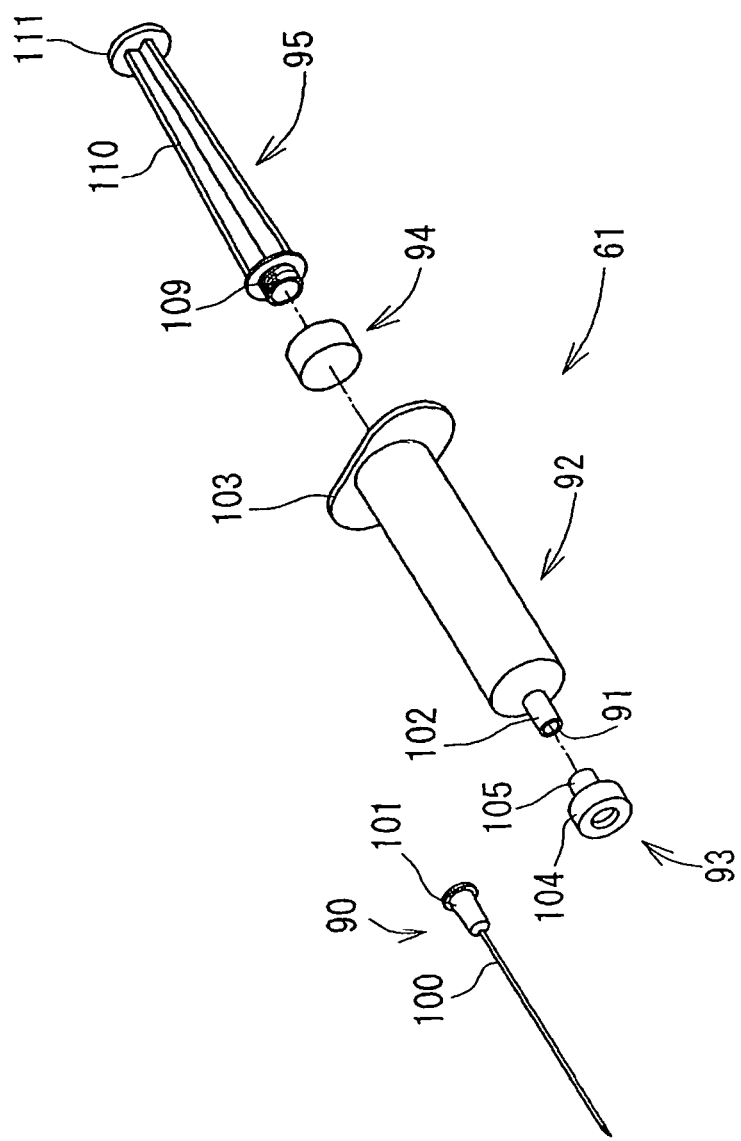
FIG. 10 is an exploded perspective view showing the external configuration of the fourth syringe 61 of the platelet-rich plasma separator according to the second embodiment of the invention.
Figure 11:
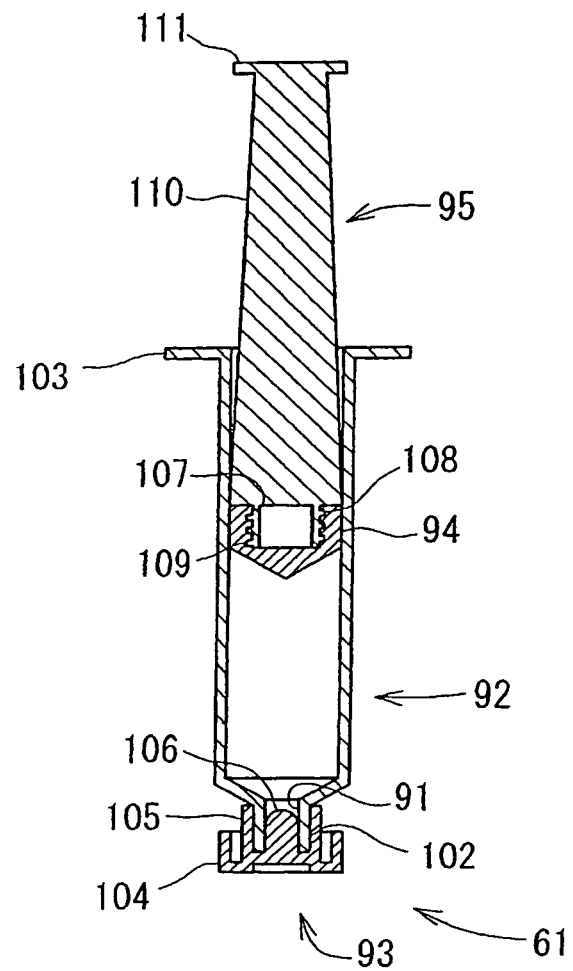
FIG. 11 is a longitudinal sectional view showing the internal configuration of the fourth syringe 61.

FIG. 8 is an exploded perspective view showing the external configuration of the third syringe 60 of the platelet-rich plasma separator according to the second embodiment of the present invention. FIG. 9 is a longitudinal sectional view showing the internal configuration of the third syringe 60. FIG. 10 is an exploded perspective view showing the external configuration of the fourth syringe 61 of the platelet-rich plasma separator according to the second embodiment of the present invention. FIG. 11 is a longitudinal sectional view showing the internal configuration of the fourth syringe 61.

The platelet-rich plasma separator according to the present invention comprises a third syringe 60 and a fourth syringe 61. The third syringe 60 is used in order to aspirate blood. Suction of blood is exemplified, in particular, by blood collection but not limited thereto, and includes the suction of the blood which has already been collected. The fourth syringe 61 is used in order to aspirate the fraction containing white blood cells, platelets, and plasma (corresponding to the second section of the invention), the fraction having been formed in the third syringe 60 by centrifugation.

As shown in FIG. 8 and FIG. 9, the third syringe 60 comprises a third syringe cylinder 63 having a third port 62 on which a blood collection needle can be mounted, a third cap 64 detachable from the third port 62, a third gasket 65 reciprocated within the third syringe cylinder 63, a first split plunger 66 provided on the third gasket 65, and a second split plunger 67 detachably connected to the first split plunger 66.

The third syringe cylinder 63 has a substantially cylindrical shape, one end portion thereof having a reduced diameter to form a needle mount 70. The internal space of the needle mount 70 communicates with the internal space of the third syringe cylinder 63. By means of the needle mount 70, the third port 62 according to the invention is formed. A blood collection needle can be mounted on the needle mount 70. The other end portion of the third syringe cylinder 63 is open without having a reduced diameter. From the other end, the first split plunger 66 and the second split plunger 67 are moved into and out of the internal space of the third syringe cylinder 63. At the other end portion of the third syringe cylinder 63, a flange 71 projecting in the peripheral direction of the third syringe cylinder 63 is formed. The flange 71 is provided for better handling, and fingers are put on the flange 71 in operating the third syringe cylinder 63, the first split plunger 66, and the second split plunger 67.

The material of the third syringe cylinder 63 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, it is common to use a molded article of polypropylene as the third syringe cylinder 63. In order to perform visual check of blood, plasma, etc. filled in the internal space of the third syringe cylinder 63, the third syringe cylinder 63 is preferably transparent or translucent. The volume of the third syringe cylinder 63 is not limited in particular. The third syringe cylinder 63 is preferably graduated so that the quantity etc. of the liquid filled in the internal space thereof can be easily known.

The third cap 64 seals the third port 62 of the third syringe cylinder 63. As shown in FIG. 8 and FIG. 9, the third cap 64 has a major diameter part 72 and a narrow diameter part 73. The narrow diameter part 73 is arranged in the space inside the major diameter part 72. The narrow diameter part 73 has a tubular shape which can be fitted onto the needle mount 70 of the third syringe cylinder 63. A plug part 74 which can be fitted in the third port 62 of the third syringe cylinder 63 is arranged in the interior of the narrow diameter part 73. The major diameter part 72 serves as a grip to be used in attaching/detaching the third cap 64 to/from the third syringe cylinder 63. Once the third cap 64 is mounted on the third syringe cylinder 63, the narrow diameter part 73 tightly fits to the outer periphery of the needle mount 70, the plug part 74 fits in the third port 62, and thus the third port 62 is sealed liquid-tightly as shown in FIG. 9.

The material of the third cap 64 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, a molded article of polypropylene or elastomer can be used as the third cap 64.

The third gasket 65 is inserted within the interior of the third syringe cylinder 63 to seal the third syringe cylinder 63 liquid-tightly. The third gasket 65 can be reciprocated within the third syringe cylinder 63 in a liquid tight manner. Reciprocation of the third gasket 65 causes a change of the volume of the liquid which can be hermetically sealed within the third syringe cylinder 63. As shown in FIG. 8, the third gasket 65 has a cylindrical shape with a diameter corresponding to the internal diameter of the third syringe cylinder 63. As shown in FIG. 9, one end face of the third gasket 65 is projected in a conical shape. The shape of this face corresponds to the shape of the innermost end of the third syringe cylinder 63. A mounting hole 75 is formed in the other end face of the third gasket 65, the side to be connected to the first split plunger 66. The mounting hole 75 is formed in the center of the circular end face of the third gasket 65. The mounting hole 75 is a circular hole having a larger diameter in the deeper portion thereof. In other words, the opening of the mounting hole 25 has a reduced diameter.

The material of the third gasket 65 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, a molded article of elastomer can be used as the third gasket 65.

The first split plunger 66 is mounted by being fitted into the third gasket 65. For the overall configuration, the first split plunger 66 has the contour of a substantially cylindrical shape that can be inserted in the internal space of the third syringe cylinder 63 and is long in the axial direction (the direction of the dotted and dashed line in FIG. 8; the vertical direction in FIG. 9) of the third syringe cylinder 63. The axial length of the first split plunger 66 is sufficiently shorter than that of the third syringe cylinder 63. Accordingly, the first split plunger 66, when mounted on the third gasket 65, will remain within the internal space of the third syringe cylinder 63 for the most distance where the third gasket 65 is reciprocated within the third syringe cylinder 63.

The first split plunger 66 has a fit-in part 76 on the tip side (third-gasket 65 side) of the shaft part 79. The fit-in part 76 is projected in the axial direction from the tip of the shaft part 79, and has a neck part 77 and a flange part 78. The neck part 77 and the flange part 78 are successively arranged in this order in the axial direction starting at the tip of the shaft part 79. The neck part 77 has a smaller contour than the flange part 78 and the shaft part 79. That is, the neck part 77 is the portion having a reduced diameter, arranged between the flange part 78 and the shaft part 79. The flange part 78 has a disk shape with its circular end face extending in the direction perpendicular to the axial direction. The shapes of the neck part 77 and the flange part 78 correspond to the shape of the mounting hole 75 of the third gasket 65, whereby the mounting hole 75 and the fit-in part 76 are fitted with each other.

The shaft part 79 has a substantially cylindrical shape. The hole 80 formed in the shaft part 79 corresponds to the insertion hole according to the present invention. The hole 80 runs through the shaft part 79 in the axial direction, reaching the flange part 78 of the fit-in part 76. Accordingly, with the third gasket 65 and the first split plunger 66 fitted together, the hole 80 serves as a path from the proximal end side (second split plunger 67 side) of the shaft part 79 to the third gasket 65. The hole 80 has a diameter large enough for the canula 100 of the second hollow needle 90 to be inserted into.

A joint part 81 is formed at the proximal end of the shaft part 79. The joint part 81 is has a smaller diameter than the shaft part 79 and is projected in the axial direction. A male screw 82 is formed in the outer periphery of the joint part 81. The hole 80 of the shaft part 79 reaches the joint part 81 and is open at the proximal end. A plug 83 is fitted in this opening. The plug 83 is an elastic member, such as rubber or elastomer, and the canula 100 of the second hollow needle 90 can be passed through the plug 83. The proximal end of the hole 80 is sealed with this plug 83. The proximal end of the shaft part 79 is equipped with a cover 84 so that the plug 83 may be covered. The cover 84 is provided in order to prevent the plug 83 from falling off. A hole 85 for exposing some portion of the plug 83 is formed in the cover 84. The hole 85 is arranged substantially on the same axis as the hole 80 of the shaft part 79. Accordingly, the canula 100 of the second hollow needle 90 inserted through the hole 85 of the cover 84 is further passed through the plug 83 into the hole 80 of the shaft part 79.

The material of the first split plunger 66 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, it is common to use a molded article of polypropylene as the first split plunger 66.

The second split plunger 67 is detachable from the first split plunger 66 in a threaded fashion. For the overall configuration, the second split plunger 67 has the contour that can be inserted in the internal space of the third syringe cylinder 63 and is long in the axial direction of the third syringe cylinder 63. With the first split plunger 66 and the second split plunger 67 connected, the total of the axial lengths thereof is longer than the axial length of the third syringe 63. Accordingly, with the third gasket 65 pushed up to the innermost end (third-port 62 side) of the third syringe cylinder 63, a portion of the second split plunger 67 is projected from the opposite end of the third syringe cylinder 63.

The second split plunger 67 has a female screw part 86, a shaft part 87, and an end plate 88. The female screw part 86 is formed on the inner periphery of the hole 89, in the portion covering the joint part 81 of the first split plunger 66. By the engagement of the female screw part 86 with the male screw 82 of the joint part 81, the first split plunger 66 and the second split plunger 67 are connected with each other on the same axis to make one plunger. In this state, the joint part 81 of the first split plunger 66 is completely covered with the female screw part 86 of the second split plunger 67. The second split plunger 67 is repeatedly detachable from the first split plunger 66. The one plunger made of the first split plunger 66 and the second split plunger 67 connected with each other corresponds to the third plunger according to the present invention.

The shaft part 87 has a cross-shaped cross section (direction perpendicular to the axial direction). The cross-sectional shape of the shaft part 87 can be suitably selected in consideration of easiness of molding, strength, etc. The female screw part 86 is arranged at one end of the shaft part 87, and the end plate 88 is arranged at the other end. The end plate 88 is a disc-shaped flat plate and is connected to the shaft part 87 perpendicular to the axial direction of the shaft part 87. The end plate 88, provided for better handling of the plunger (the third plunger) formed by the first split plunger 66 and the second split plunger 67, is pressed by a finger when the third plunger is pushed into the third syringe cylinder 63, and serves a grip when the third plunger is pulled outwardly from the third syringe cylinder 63.

The material of the second split plunger 67 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, it is common to use a molded article of polypropylene as the second split plunger 67.

As shown in FIG. 10 and FIG. 11, the fourth syringe 61 comprises a second hollow needle 90, a fourth syringe cylinder 92 having a fourth port 91 on which the second hollow needle 90 can be mounted, a fourth cap 93 detachable from the fourth port 91, a fourth gasket 94 reciprocated within the fourth syringe cylinder 92, and a fourth plunger 95 provided detachably on the fourth gasket 94.

The second hollow needle 90 has a canula 100 with a blade face formed at the tip of the hollow tube, and a hub 101 connected to the proximal end of the canula 100. The axial length of the canula 100 is set to be the length necessary for the canula 100 to be passed through the hole 80 of the first split plunger 66 of the third syringe 60 and further through the third gasket 65. The hub 101 has a substantially cylindrical shape and is set to have an internal diameter and an axial length necessary to be fitted onto the needle mount 102 of the fourth syringe cylinder 92. The end portion of the hub 101 to which the proximal end of the canula 100 is connected is closed except the portion that is connected to the canula 100. The canula 100 and the hub 101 are fixed together by means of adhesives etc. The end portion of the hub 101 which is to be connected to the needle mount 102 is open. The opening at the proximal end of the canula 100 communicates with the internal space of the hub 101. Accordingly, the liquid etc. entering the opening at the tip of the canula 100 and advancing through the canula 100 flows through the opening at the proximal end of the canula 100 into the internal space of the hub 101. This internal space communicates with the fourth port 91 by the hub 101 being fitted onto the needle mount 102.

The 4th syringe cylinder 92 has a substantially cylindrical shape and is of a size that can be advanced into the internal space of third syringe cylinder 63. One end portion of the fourth syringe cylinder 92 has a reduced diameter to form a needle mount 102. The internal space of the needle mount 102 communicates with the internal space of the fourth syringe cylinder 92. By means of the needle mount 102, the fourth port 91 according to the present invention is formed. A second hollow needle 90 can be mounted on the needle mount 102. The other end portion of the fourth syringe cylinder 92 is open without having a reduced diameter. From the other end portion, the fourth plunger 95 is moved into and out of the internal space of the fourth syringe cylinder 92. At the other end portion of the fourth syringe cylinder 92, a flange 103 projecting in the peripheral direction of the fourth syringe cylinder 92 is formed. The flange 103 is provided for better handling, and fingers are put on the flange 103 in operating the fourth syringe cylinder 92 and the fourth plunger 95.

The material of the fourth syringe cylinder 92 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, it is common to use a molded article of polypropylene as the fourth syringe cylinder 92. In order to perform visual check of plasma, etc. filled in the internal space of the fourth syringe cylinder 92, the fourth syringe cylinder 92 is preferably transparent or translucent. The volume of the fourth syringe cylinder 92 is not limited in particular. The fourth syringe cylinder 92 is preferably graduated so that the quantity etc. of the liquid filled in the internal space thereof can be easily known.

The fourth cap 93 seals the fourth port 91 of the fourth syringe cylinder 92. As shown in FIG. 10 and FIG. 11, the fourth cap 93 has a major diameter part 104 and a narrow diameter part 105. The narrow diameter part 105 is arranged in the space inside the major diameter part 104. The narrow diameter part 105 has a tubular shape which can be fitted onto the needle mount 102 of the fourth syringe cylinder 92. A plug part 106 which can be fitted in the fourth port 91 of the fourth syringe cylinder 92 is arranged in the interior of the narrow diameter part 105. The major diameter part 104 serves as a grip to be used in attaching/detaching the fourth cap 93 to/from the fourth syringe cylinder 92. Once the fourth cap 93 is mounted on the fourth syringe cylinder 92, the narrow diameter part 105 tightly fits to the outer periphery of the needle mount 102, the plug part 106 fits in the fourth port 91, and thus the fourth port 91 is sealed liquid-tightly as shown in FIG. 11.

The material of the fourth cap 93 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, a molded article of polypropylene or elastomer can be used as the fourth cap 93.

The fourth gasket 94 is inserted within the interior of the fourth syringe cylinder 92 to seal the fourth syringe cylinder 92 liquid-tightly. The fourth gasket 94 can be reciprocated within the fourth syringe cylinder 92 in a liquid tight manner. Reciprocation of the fourth gasket 94 causes a change of the volume of the liquid which can be hermetically sealed within the fourth syringe cylinder 92. As shown in FIG. 10, the fourth gasket 94 has a cylindrical shape with a diameter corresponding to the internal diameter of the fourth syringe cylinder 92. As shown in FIG. 11, one end face of the fourth gasket 94 is projected in a conical shape. The shape of this face corresponds to the shape of the innermost end of the fourth syringe cylinder 92. A mounting hole 107 is formed in the other end face of the fourth gasket 94, the side to be connected to the fourth plunger 95. The mounting hole 107 is formed in the center of the circular end face of the fourth gasket 94. The mounting hole 107 is a circular hole. A female screw 108 is formed in the inner periphery of the mounting hole 107.

The material of the fourth gasket 94 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, a molded article of elastomer can be used as the fourth gasket 94.

The fourth plunger 95 is detachable from the fourth gasket 94 in a threaded fashion. For the overall configuration, the fourth plunger 95 has the contour that can be inserted in the internal space of the fourth syringe cylinder 92 and is sufficiently longer than the axial (the direction of the dotted and dashed line in FIG. 10; the vertical direction in FIG. 11) length of the fourth syringe cylinder 92. Accordingly, with the fourth gasket 94 pushed up to the innermost end (fourth-port 91 side) of the fourth syringe cylinder 92, a portion of the fourth plunger 95 is projected from the opposite end of the fourth syringe cylinder 92.

The fourth plunger 95 has a male screw part 109, an shaft part 110, and an end plate 111. The male screw part 109 is threaded into the mounting hole 107 of the fourth gasket 94. The female screw 108 of the mounting hole 107 engages the male screw part 109. Thereby, the fourth plunger 95 is attached/detached to/from the fourth gasket 94 in a threaded fashion. This attachment and detachment can be performed repeatedly.

The shaft part 110 has a cross-shaped cross section (direction perpendicular to the axial direction). The cross-sectional shape of the shaft part 110 can be suitably selected in consideration of easiness of molding, strength, etc. The male screw part 109 is arranged at one end of the shaft part 110, and the end plate 111 is arranged at the other end. The end plate 111 is a disc-shaped flat plate and is connected to the shaft part 110 perpendicular to the axial direction of the shaft part 110. The end plate 111, provided for better handling of the fourth plunger 95, is pressed by a finger when the fourth plunger 95 is pushed into the fourth syringe cylinder 92, and serves a grip when the fourth plunger 95 is pulled outwardly from the fourth syringe cylinder 92.

The material of the fourth plunger 95 is not limited in particular as long as it can be sterilized by gamma radiation, and it can be glass, synthetic resins, etc. Taking into consideration that a platelet-rich plasma separator is used as a disposal article and that it is subjected to gamma radiation sterilization, it is common to use a molded article of polypropylene as the fourth plunger 95.

In consideration of obtaining the platelet-rich plasma suitable for regeneration medicine, of the members that form a platelet-rich plasma separator, at least the third syringe cylinder 63, the third cap 64, the third gasket 65, the second hollow needle 90, the fourth syringe cylinder 92, the fourth cap 93, and the fourth gasket 94, which will be in contact with the collected blood, are sterilized by gamma radiation. Provision of the third syringe 60 and the fourth syringe 61 as a kit hermetically sealed in a sterilized package would improve the user-friendliness of the platelet-rich plasma separator.

The configuration of each member of the third syringe 60 and the fourth syringe 61 according to this embodiment is merely exemplary, and part of the configuration of each member may be modified to a known configuration without departing from the spirit or scope of the invention. For example, the blood collection needle may be directly or via an extension tube etc. mounted on the needle mount 70 of the third syringe 60. Likewise, the second hollow needle 90 may be directly or via an extension tube etc. mounted on the needle mount 102 of the fourth syringe 61.

Figure 13:
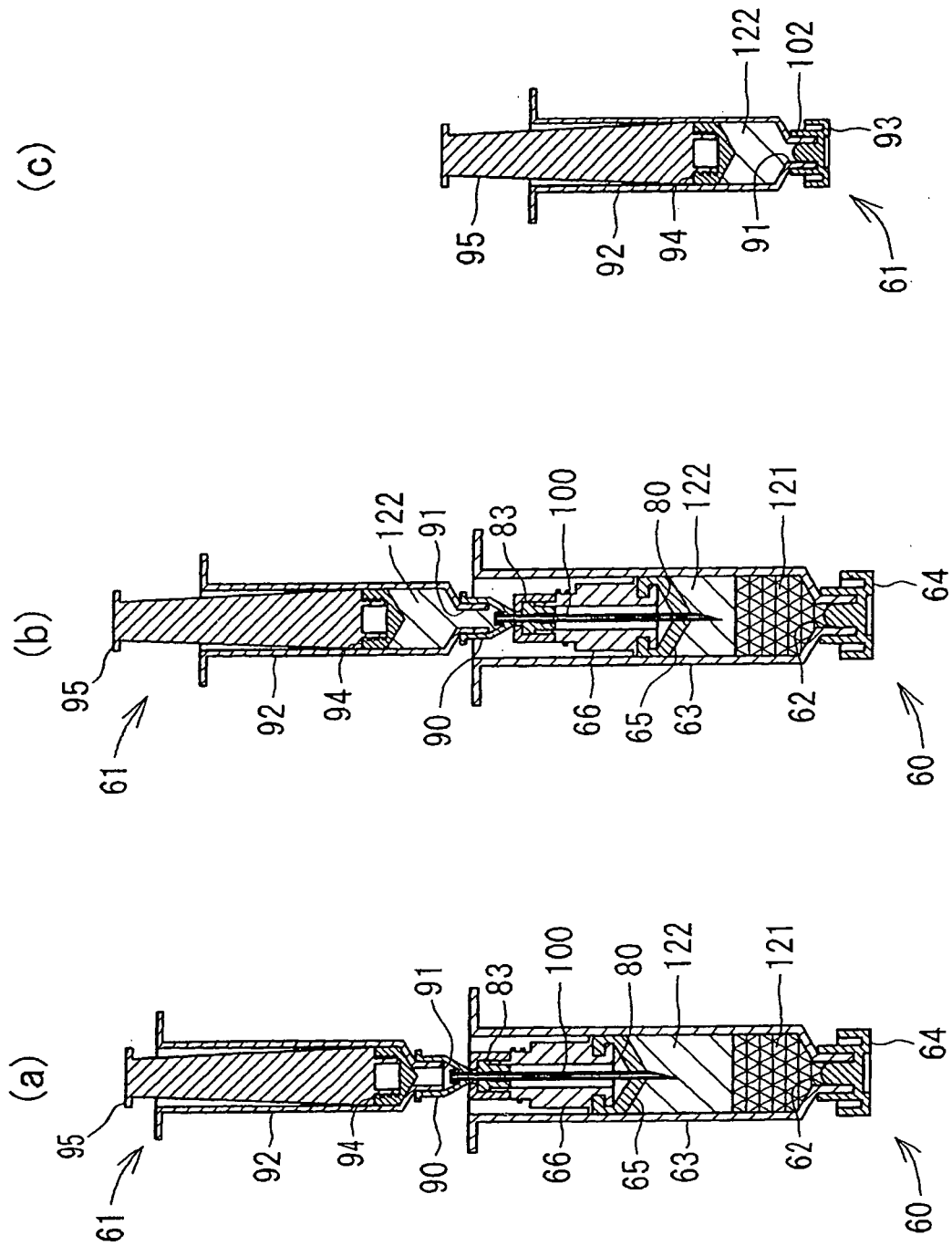
FIG. 13 is a cross-sectional view showing the state of the platelet-rich plasma separator in each step of the platelet-rich plasma separation method according to the second embodiment.
Figure 14:
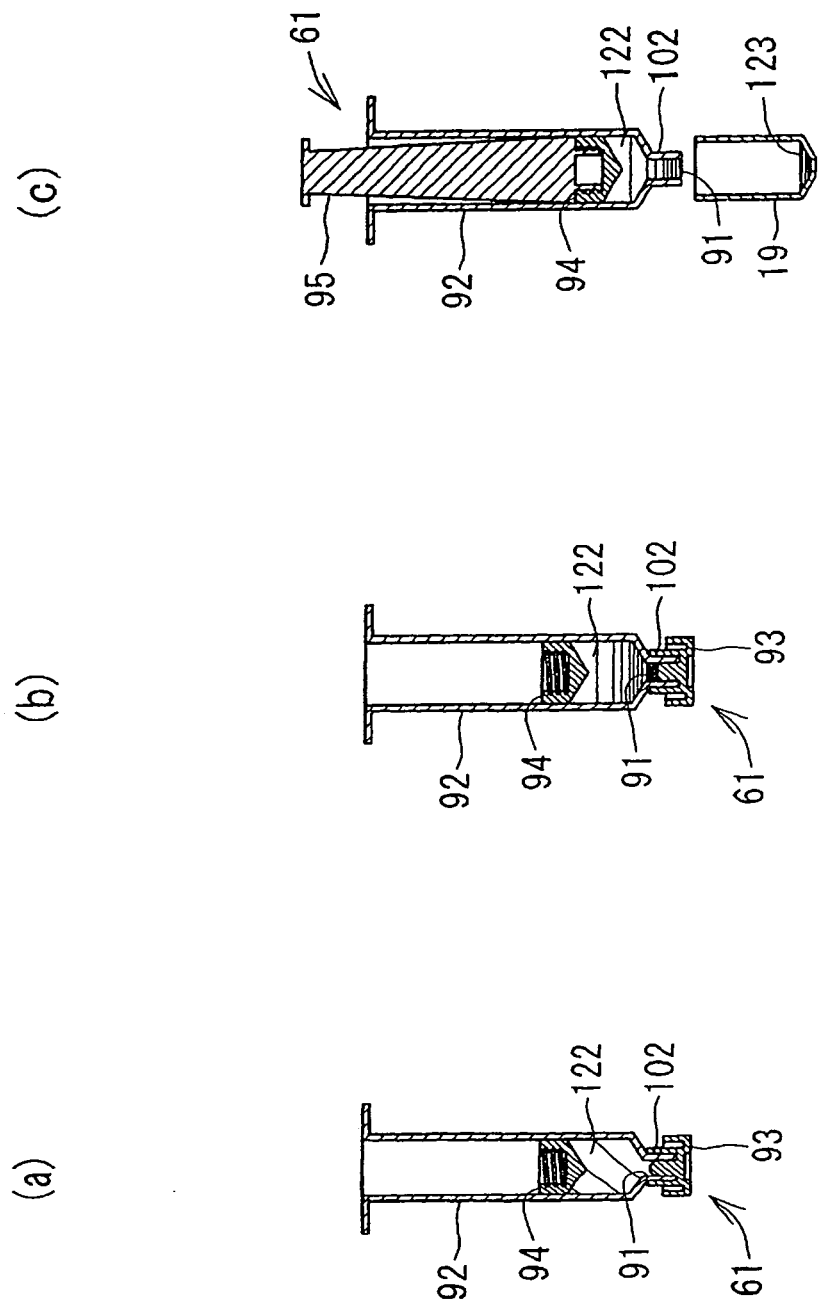
FIG. 14 is a cross-sectional view showing the state of the platelet-rich plasma separator in each step of the platelet-rich plasma separation method according to the second embodiment.

The platelet-rich plasma separation method according to the present invention will now be explained. The platelet-rich plasma separation method according to the embodiment is performed using said platelet-rich plasma separator and consists mainly of six steps. In the seventh step, the third port 62 of the third syringe cylinder 63 filled with collected blood 120 is sealed. In the eighth step, the blood 120 in the third syringe cylinder 63 is centrifuged into a first section 121 containing red blood cells and a second section 122 containing white blood cells, platelets and plasma, with the third-port 62 side of the third syringe cylinder 63 set as the direction of centrifugal movement. In the ninth step, the second hollow needle 90 is passed through the third gasket 65 in the third syringe cylinder 63, to aspirate the second section 122 into the fourth syringe cylinder 92. In the tenth step, the fourth port 91 of the fourth syringe cylinder 92 filled with the second section 122 is sealed. In the eleventh step, the second section 122 in the fourth syringe cylinder 92 is centrifuged, with the fourth-port 91 side of the fourth syringe cylinder 92 set as the direction of centrifugal movement. In the twelfth step, the fourth gasket 94 in the fourth syringe cylinder 92 is moved to discharge the platelet-rich plasma 123 out of the centrifuged second section 122 through the fourth port 91. These steps will now be explained in detail using FIG. 12 to FIG. 14. Each one of FIG. 12 to FIG. 14 is a cross-sectional view showing the state of the platelet-rich plasma separator in each step of the platelet-rich plasma separation method.

Figure 12:
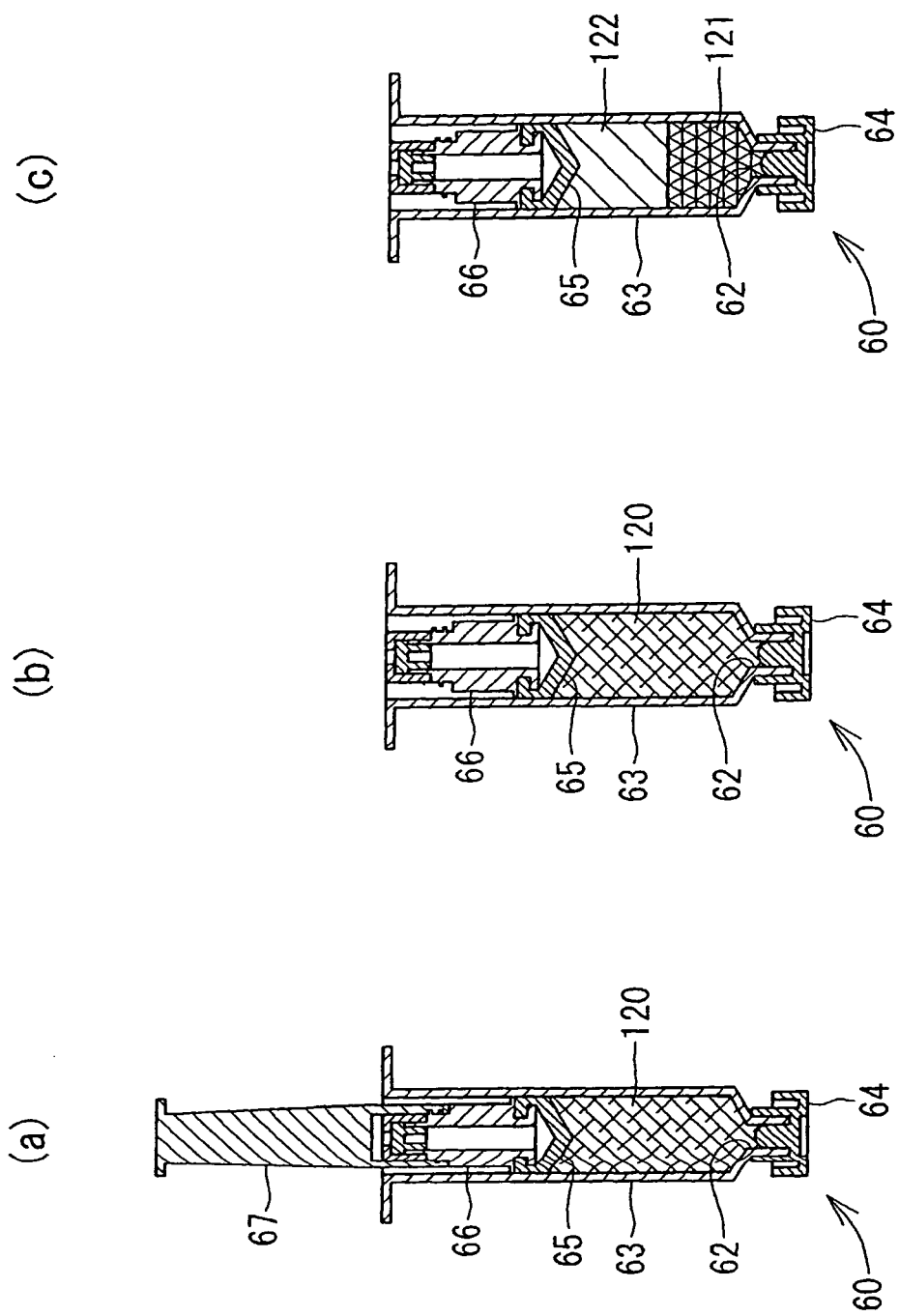
FIG. 12 is a cross-sectional view showing the state of the platelet-rich plasma separator in each step of the platelet-rich plasma separation method according to the second embodiment.

In the seventh step, the third port 62 of the third syringe cylinder 63 is sealed with the third cap 64 to hermetically seal the third syringe cylinder 63 as shown in FIG. 12 (a). The third syringe 60 is used for blood collection. In collecting blood, a blood collection needle is mounted on the third port 62 of the third syringe cylinder 63. Of course, the blood collection needle may be mounted on the third port 62 via an extension tube etc. The first split plunger 66 and the second split plunger 67 are connected with each other. Blood collection is performed by a usual method, and thus the detailed explanation is omitted. By this blood collection, the third syringe cylinder 63 is filled with blood 120. The blood 120 is whole blood, containing red blood cells, white blood cells, platelets, plasma, etc. After the blood collection, the blood collection needle is removed from the third port 62 of the third syringe cylinder 63, and then the third port 62 is sealed with the third cap 64. Thereby, the third syringe cylinder 63 is in a hermetically sealed state as shown in FIG. 12 (a).

In the eighth step, the first centrifugation is performed using the hermetically sealed syringe. Prior to this centrifugation, the second split plunger 67 is removed from the first split plunger 66 as shown in FIG. 12 (b). This prevents the second split plunger 67 from being projected from the third syringe cylinder 63, thereby achieving easier handling of the third syringe cylinder 63 at the time of centrifugation. Moreover, the second split plunger 67 cannot be operated carelessly during the centrifugation. Further, the weight of the second split plunger 67 does not act on the third gasket 65 during the centrifugation, thereby reducing the risk of the third cap 64 coming off the third syringe cylinder 63.

In this centrifugation, the third-port 62 side of the third syringe cylinder 63 is set as the direction of centrifugal movement. Here, the "direction of centrifugal movement" is the direction to which centrifugal force is applied during the centrifugation and, in general, downward. The centrifugation in the eighth step is weak centrifugation. Weak centrifugation, which is commonly used in the centrifugation of blood, is defined, in general, as "centrifugation that separates whole blood into red blood cells and others (white blood cells, platelets, plasma)" (see Nonpatent Literature 1). Specifically, the centrifugation under the centrifugation condition of approximately 500 to 2500 rpm is considered as weak centrifugation. Since a common type of centrifuge is used here, the detailed description is omitted.

By this centrifugation, the blood 120 hermetically sealed in the third syringe cylinder 63 is separated into a first section 121 and a second section 122. The first section 121 is a fraction containing red blood cells. The second section 122 is a fraction containing white blood cells, platelets, and plasma. As shown in FIG. 12 (c), the first section 121 is separated toward the direction of centrifugal movement, that is, toward the lower part of the third syringe cylinder 63, by centrifugation.

In the ninth step, the second section 122 in the third syringe cylinder 63 is aspirated into the fourth syringe cylinder 92. After the first centrifugation, the second hollow needle 90 mounted on the fourth port 91 of the fourth syringe 92 is inserted through the hole 80 of the first split plunger 66 as shown in FIG. 13 (a). Since the proximal end of the hole 80 is sealed with the plug 83, the canula 100 of the second hollow needle 90 is first passed through the plug 83 into the hole 80. The canula 100 is further advanced through the hole 80, and then the tip of the canula 100 comes out of the hole 80 to reach the third gasket 65. The canula 100 is further advanced to be passed through the third gasket 65. As a result, the tip of the canula 100 of the second hollow needle 90 reaches the second section 122 in the third syringe cylinder 63. In that state, the fourth plunger 95 of the fourth syringe 61 is pulled outwardly from the fourth syringe cylinder 92 to aspirate the second section 122 in the third syringe cylinder 63 into the fourth syringe cylinder 92. When the second hollow needle 90 is mounted on the fourth port 91 via an extension tube etc. as well, the second hollow needle 90 is inserted through the hole 80 of the first split plunger 66 to be passed through the third gasket 65 in the same manner as above.

As shown in FIG. 13 (b), as the fourth plunger 95 is pulled outwardly from the fourth syringe cylinder 92, the second section 122 in the third syringe cylinder 63 is aspirated into the fourth syringe cylinder 92 and the third gasket 65 is moved within the third syringe cylinder 63 toward the third-port 62 side. Since the canula 100 of the second hollow needle 90 has been passed through the third gasket 65 and the plug 83, the friction force among them causes the fourth syringe cylinder 92 to be advanced into the third syringe cylinder 63 with the movement of the third gasket 65. Thereby, the suction of the second section 122 from the third syringe cylinder 63 into the fourth syringe cylinder 92 is performed smoothly and continuously. Although the first section 121 and small quantities of the second section 122 will remain in the third syringe cylinder 63 at this time, they will be disposed or used for other purposes.

By employing weak centrifugation in the eighth step, the blood 120 can be separated into the first section 121 and the second section 122, and the platelets can be distributed almost uniformly in the second section 122 as well. That is, the platelets fail to concentrate near the boundary of the first section 121. This can reduce the loss of platelets which would be caused by the slight loss of the second section 122 generated at the time of suction of the second section 122 from the third syringe cylinder 63 into the fourth syringe cylinder 92.

In the tenth step, the fourth port 91 of the fourth syringe cylinder 92 is sealed with the fourth cap 93 so that the fourth syringe cylinder 92 is kept in a hermetically sealed state. As shown in FIG. 13 (b), the fourth syringe cylinder 92 is filled only with the second section 122 aspirated from the third syringe cylinder 63. When the second hollow needle 90 mounted on the fourth syringe 61 is pulled out of the first split plunger 66 with the fourth plunger 95 fixed, the third gasket 65 in the hermetically sealed third syringe cylinder 63 remains stationary without moving in the third syringe cylinder 63. Then, the second hollow needle 90 is removed from the fourth syringe cylinder 92 to seal the fourth port 91 with the fourth cap 93 as shown in FIG. 13 (c). As a result, the fourth syringe cylinder 92 is hermetically sealed, filled with the second section 122.

In the eleventh step, the second centrifugation is performed using the fourth syringe cylinder 92 hermetically sealed. Prior to this centrifugation, the fourth plunger 95 is removed from the fourth gasket 94 as shown in FIG. 14 (a). This prevents the fourth plunger 95 from being projected from the fourth syringe cylinder 92, thereby achieving easier handling of the fourth syringe cylinder 92 at the time of centrifugation. Moreover, the fourth plunger 95 cannot be operated carelessly during the centrifugation. Further, the weight of the fourth plunger 95 does not act on the fourth gasket 94 during the centrifugation, thereby reducing the risk of the fourth cap 93 coming off the fourth syringe cylinder 92.

In this centrifugation, the fourth-port 91 side of the fourth syringe cylinder 92 is set as the direction of centrifugal movement. The centrifugation in the eleventh step is strong centrifugation. Strong centrifugation, which is commonly used in the centrifugation of blood, is defined, in general, as "centrifugation that separates platelets, white blood cells and remaining red blood cells from plasma" (see Nonpatent Literature 1). In the present invention, the centrifugation that condenses platelets in the lower part of the second section is called strong centrifugation. Specifically, the centrifugation under the centrifugation condition of approximately 3000 to 4000 rpm is considered as strong centrifugation. By this centrifugation, the second section 122 is centrifuged, and platelets are moved toward the direction of centrifugal movement, that is, toward the lower part of the fourth syringe cylinder 92 as shown in FIG. 14 (b). By employing the strong centrifugation, high-concentration PRP 123 can be separated from the second section 122. In FIG. 14 (b), the higher the density of the horizontal lines in the second section 122 is, the higher the platelet concentration. In fact, in the centrifuged second section 122, that the platelets have moved towards the lower part can be confirmed visually by means of the gradation from substantial transparence to deep yellow formed from the upper part towards the lower part.

In the twelfth step, the PRP 123 is discharged from the fourth syringe cylinder 92. After the completion of the centrifugation, the fourth plunger 95 is mounted on the fourth gasket 94 as shown in FIG. 14 (c). Thereby, the fourth gasket 94 can be moved easily. Then the fourth cap 93 is removed from the fourth syringe cylinder 92 to open the fourth port 91. In this state, the fourth plunger 95 is operated to move the fourth gasket 94 toward the fourth port 91 side. By the second centrifugation, the platelets in the second section 122 are centrifugally moved, whereby the second section 122 is separated into an upper portion substantially consisting only of the supernatant, that is, the plasma component, and a lower portion (fourth port 91 side) containing PRP 123 containing a large number of platelets. Accordingly, the PRP 123 is discharged from the fourth port 91 with the movement of the fourth gasket 94. The discharged PRP 123 is received in a sterilized container 19. Thereby, the PRP 123 is separated from the collected blood 120.

There is not necessarily a clear definition of the platelet concentration in PRP 123. However, suppose, for example, the platelet concentration is expressed in terms of the platelet count in 1 mL, the platelet concentration of the PRP 123 would be 3-7 times higher than that of the collected whole blood. On the other hand, in the platelet-rich plasma separation method according to the invention, a predetermined amount taken from the fourth port 91 side of the second section 122 centrifuged in the eleventh step may be defined as the PRP 123. By the platelet-rich plasma separation method according to this embodiment, approximately 1 mL of the PRP 123 can be obtained from approximately 10 mL of the blood 120, for example.

In this embodiment, the PRP 123 in the twelfth step is directly discharged from the fourth port 91 of the fourth syringe cylinder 92 into the container 19 etc. However, it should be noted that for prevention of infection, etc., a tube and a three way stopcock, etc. may be connected to the fourth port 91 of the fourth syringe cylinder 92 so that the PRP 123 to be discharged can be aspirated in another syringe.

Thus, according to the platelet-rich plasma separator and the platelet-rich plasma separation method according to the invention, PRP 123 can be obtained from the blood 120 by centrifuging the third syringe 60 used for blood collection. Thereby, separation of PRP 123 can be realized using a small number of gamma radiation sterilized instruments. Moreover, by using two syringes 60, 61, the first section 121 and the second section 122 can be reliably separated, whereby high-concentration PRP 123 can be obtained.

The present invention is applicable to platelet-rich plasma separators and platelet-rich plasma separation methods for obtaining PRP by centrifuging whole blood.

What is claimed is:

1. A platelet-rich plasma separator comprising a first syringe used to aspirate blood and a second syringe used to aspirate a centrifuged section containing platelets and plasma from the first syringe,
wherein said first syringe comprises:
a first syringe cylinder having a first port on which a blood collection needle can be mounted,
a first cap detachable from said first port,
a first gasket for sealing said first syringe cylinder liquid-tightly, which first gasket is reciprocated within the first syringe cylinder, and
a first plunger provided detachably on said first gasket, wherein the first gasket has a mounting opening for removably mounting the first plunger, said mounting opening extending into the first gasket without extending through the first gasket; and
wherein said second syringe comprises:
a first hollow needle, which can be passed through said first gasket,
a second syringe cylinder having a second port on which said first hollow needle can be mounted,
a second cap detachable from said second port,
a second gasket for sealing said second syringe cylinder liquid-tightly, which second gasket is reciprocated within the second syringe cylinder;
a second plunger provided detachably on said second gasket, and
a guide piece formed on the second syringe cylinder around the second port and extending beyond the distal tip of the second port and into said mounting opening of said first syringe, the guide piece having a diameter allowing the guide piece to fit into the mounting opening.

2. The platelet-rich plasma separator according to claim 1 wherein said first plunger is detachable from said first gasket in a threaded fashion and said second plunger is detachable from said second gasket in a threaded fashion.

3. The platelet-rich plasma separator according claim 1 wherein said first syringe and said second syringe are provided in a hermetically sealed sterilized package.

4. A platelet-rich plasma separator comprising a third syringe used to aspirate blood and a fourth syringe used to aspirate a centrifuged section containing platelets and plasma from the third syringe,
wherein said third syringe comprises:
a third syringe cylinder having a third port on which a blood collection needle can be mounted;
a third cap detachable from said third port;
a third gasket for sealing said third syringe cylinder liquid-tightly, which third gasket is reciprocated within the third syringe cylinder;
a first split plunger provided on said third gasket and having an insertion hole sealed at a distal end with the third gasket, the first split plunger comprising a first part at a distal end toward the third gasket, a shaft part proximal to the first part, and a joint part proximal to the shaft part;
a plug which seals the insertion hole at a proximal end; and
a second split plunger detachably connected to said first split plunger at said joint part; and
wherein said fourth syringe comprises:
a second hollow needle of sufficient length to penetrate the plug, pass through the insertion hole of said first split plunger, and penetrate through said third gasket into said third syringe cylinder;
a fourth syringe cylinder having a fourth port on which said second hollow needle can be mounted;
a fourth cap detachable from said fourth port;
a fourth gasket for sealing said fourth syringe cylinder liquid-tightly, which fourth gasket is reciprocated within the fourth syringe cylinder; and
a fourth plunger provided detachably on said fourth gasket.

5. The platelet-rich plasma separator according to claim 4 wherein said second split plunger is detachable from said first split plunger in a threaded fashion and said fourth plunger is detachable from said fourth gasket in a threaded fashion.

6. The platelet-rich plasma separator according to claim 4 wherein said third syringe and said fourth syringe are provided in a hermetically sealed sterilized package.

* * * * *